United States Patent
Zhang et al.

(10) Patent No.: US 10,556,124 B2
(45) Date of Patent: Feb. 11, 2020

(54) SYSTEM AND METHOD FOR OPTIMIZING A TREATMENT PLAN FOR IRRADIATION THERAPY USING MULTI-CRITERIA OPTIMIZATION (MCO)

(71) Applicant: University of Maryland, Baltimore, Baltimore, MD (US)

(72) Inventors: Hao H. Zhang, Potomac, MD (US); Gokhan Kirlik, Baltimore, MD (US); Warren D. D'Souza, Timonium, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 356 days.

(21) Appl. No.: 15/445,073

(22) Filed: Feb. 28, 2017

(65) Prior Publication Data
US 2017/0246477 A1 Aug. 31, 2017

Related U.S. Application Data

(60) Provisional application No. 62/301,106, filed on Feb. 29, 2016.

(51) Int. Cl.
*A61N 5/10* (2006.01)

(52) U.S. Cl.
CPC ......... *A61N 5/1031* (2013.01); *A61N 5/1039* (2013.01); *A61N 5/1047* (2013.01)

(58) Field of Classification Search
CPC ........ A61N 5/103–1039; A61N 5/1047; A61N 2005/1032–1041
See application file for complete search history.

(56) References Cited

U.S. PATENT DOCUMENTS

| | | | |
|---|---|---|---|
| 2004/0071261 A1* | 4/2004 | Earl | A61N 5/1031 378/65 |
| 2010/0020931 A1* | 1/2010 | Otto | A61B 6/5241 378/65 |
| 2012/0136194 A1* | 5/2012 | Zhang | A61N 5/103 600/1 |

(Continued)

OTHER PUBLICATIONS

Beaulieu, F., et al., Automatic Generation of Anatomy-Based MLC Fields in Aperture-based IMRT, "Med. Phys." pp. 1539-1545, vol. 31, Issue 6 (2004).

(Continued)

*Primary Examiner* — Catherine B Kuhlman
(74) *Attorney, Agent, or Firm* — Beusse Wolter Sanks & Maire; Eugene J. Molinelli

(57) ABSTRACT

A method and apparatus is presented for optimizing a treatment plan for irradiation therapy. The method includes defining a single objective function based on a plurality of objective functions that are each associated with a plurality of tissue types within a subject, upper and lower bounds for each objective function and a plurality of apertures. The method also includes determining a radiation dose delivered to voxels of each tissue type based on minimizing the single objective function based on the plurality of apertures with initial values at each angle. The method also includes delivering a beam of radiation with controlled intensity and beam cross-sectional shape at each angle based on the plurality of apertures.

19 Claims, 17 Drawing Sheets

(56) References Cited

U.S. PATENT DOCUMENTS

2013/0197878 A1* 8/2013 Fiege ............... A61N 5/1031 703/2
2014/0206923 A1* 7/2014 Hirayama ............ A61N 5/1031 600/1

OTHER PUBLICATIONS

Bokrantz, R., Forsgren, A., An algorithm for approximating convex pareto surfaces based on dual techniques, "Informs Journal on Computing", pp. 377-393, vol. 25, Issue 2 (2013).
Bokrantz, R. Distributed approximation of pareto surfaces in multicriteria radiation therapy treatment planning, "Phys. In Med. Biol". pp. 3501-3516, vol. 58 (2013).
Breedveld, et al., The equivalence of multi-criteria methods for radiotherapy plan optimization, "Phys. Med. Biol." pp. 7199-7209, vol. 54 (2009).
Cotrutz, C., et al., A multiobjective gradient-based dose optimization algorithm for external beam conformal radiotherapy, "Phys. Med. Biol." pp. 2161-2175, vol. 46 (2001).
Craft, D., et al., Approximating convex pareto surfaces in multiobjective radiotherapy planning, "Med. Phys." pp. 3399-3407, vol. 33, Issue 9 (2006).
Craft, D., Bortfeld, T., How many plans are needed in an IMRT multiobjective plan database, "Phys. Med. Biol.", pp. 2785-2796, vol. 53 (2008).
Craft, D., Monz, M., Simultaneous navigation of multiple pareto surfaces, with an application to multicriteria IMRT planning with multiple beam angle configurations, "Med. Phys." pp. 736-741, vol. 37, Issue 2 (2010).
Craft, D., Multi-criteria optimization methods in radiation therapy planning: a review of technologies and directions, "Massachusetts General Hospital", pp. 1-16 (2013).
D'Amico, A., et al., Biochemical outcome after radical prostatectomy external beam radiation therapy or interstitial radiation therapy for clinically localized prostate cancer, "JAMA", pp. 969-974, vol. 280, Issue 11 (1998).
Dryzmala, R., et al., Dose-Volume histograms, "Int. J. Radiation Oncology Biol. Phys." pp. 71-78, vol. 21 (1991).
Ehrgott, M., A discussion of scalarization techniques for multiple objective integer programming, "Ann. Oper. Res.", pp. 343-360, vol. 147 (2006).
Ehrgott, M., et al., Decomposition of matrices and static multileaf collimators: a survey, "Springer", pp. 1-23 (2008).
Ehrgott, M., et al., Mathematical optimization in intensity modulated radiation therapy, "Ann. Oper. Res." pp. 309-365, vol. 175 (2010).
Holder, A., Designing radiotherapy plans with elastic constraints and interior point methods, "Health Care Management Science", pp. 5-16, vol. 6 (2003).
Hong, T., et al., Multicriteria optimization in intensity-modulated radiation therapy treatment planning for locally advanced cancer of the pancreatic head, "Int. J. Radiation Oncology Biol. Phys." pp. 1208-1214, vol. 72, Issue 4 (2008).
Lee, E., et al., Integer programming applied to intensity-modulated radiation therapy treatment planning, "ann. op. res.", pp. 165-181, vol. 119 (2003).
Lin, J., On min-norm and min-max methods of multi-objective optimization, "Math. Program., Ser. A" pp. 1-33, vol. 103 (2005).
Luan, S., et al. A new MLC segmentation algorithm/software for step-and-shoot IMRT delivery, "Medical Pysh." pp. 695-707, vol. 31, Issue 4 (2004).
Men, C., et al., An exact approach to direct aperture optimization in IMRT treatment planning, "Phys. Med. Biol." p. 7333, vol. 52, Issue 24 (2007).
Miettinen, K., Makela, M., On scalarizing functions in multiobjective optimization, "OR Spectrum", pp. 193-213, vol. 24, Issue 2 (2002).
Monz, M., Pareto navigation-interactive multiobjective optimisation and its application in radiotherapy planning, "Phd Thesis, Dept. Math. Tech. Univ. Kaiserslautern" (2006).
Zhang, H., et al., Beam controlled arc therapy—a delivery concept for stationary targets, "Phys. Med. Biol.", p. 7117, vol. 58, Issue 20 (2013).
Monz, M. et al., Pareto navigation algorithmic foundation of interactive multi-criteria IMRT planning, "Phys. Med. Biol." p. 985, vol. 53, Issue 4 (2008).
Preciado-Walters, F., et al., Column generation for IMRT cancer therapy optimization with implementable segments, "Ann. op. res." pp. 65-79, vol. 148 (2006).
Rennen, G., et al., Enhancement of sandwich algorithms for approximating higher-dimensional convex pareto sets, "Informs journal on computing", pp. 493-517, vol. 23, Issue 4 (2011).
Romeijn, H., et al., A novel linear programming approach to fluence map optimization for intensity modulated radiation therapy treatment planning, "Phys. Med. Biol.", p. 3521, vol. 48, Issue 21 (2003).
Romeijn, H., et al., A column generation approach to radiation therapy treatment planning using aperture modulation, "Siam J. Optimization", pp. 838-862, vol. 15, Issue 3 (2005).
Taskin, Z., et al., Optimal multileaf collimator leaf sequencing in IMRT treatment planning, "Operations Res.", pp. 674-690, vol. 58, Issue 3 (2010).
Thieke, C., et al., A new concept for interactive radiotherapy planning with multicriteria optimization: first clinical evaluation, "Radiotherapy and oncology", pp. 292-298, vol. 85, Issue 2 (2007).
Wierzbicki, A., A methodological approach to comparing parametric characterizations of efficient solutions, "Large-scale modelling and interactive decision analysis", pp. 27-45 (1986).
Zadeh, L., Optimality and non-scalar-valued performance criteria, "IEEE Transactions on Automatic Control", pp. 59-60, vol. 8 (1963).

* cited by examiner

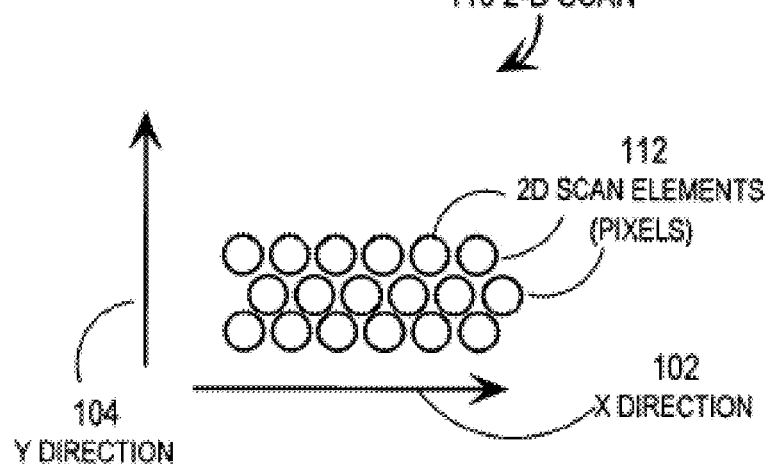
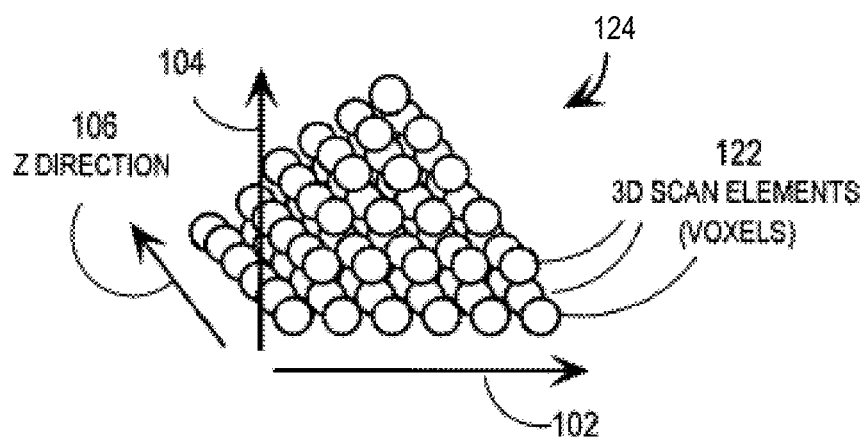

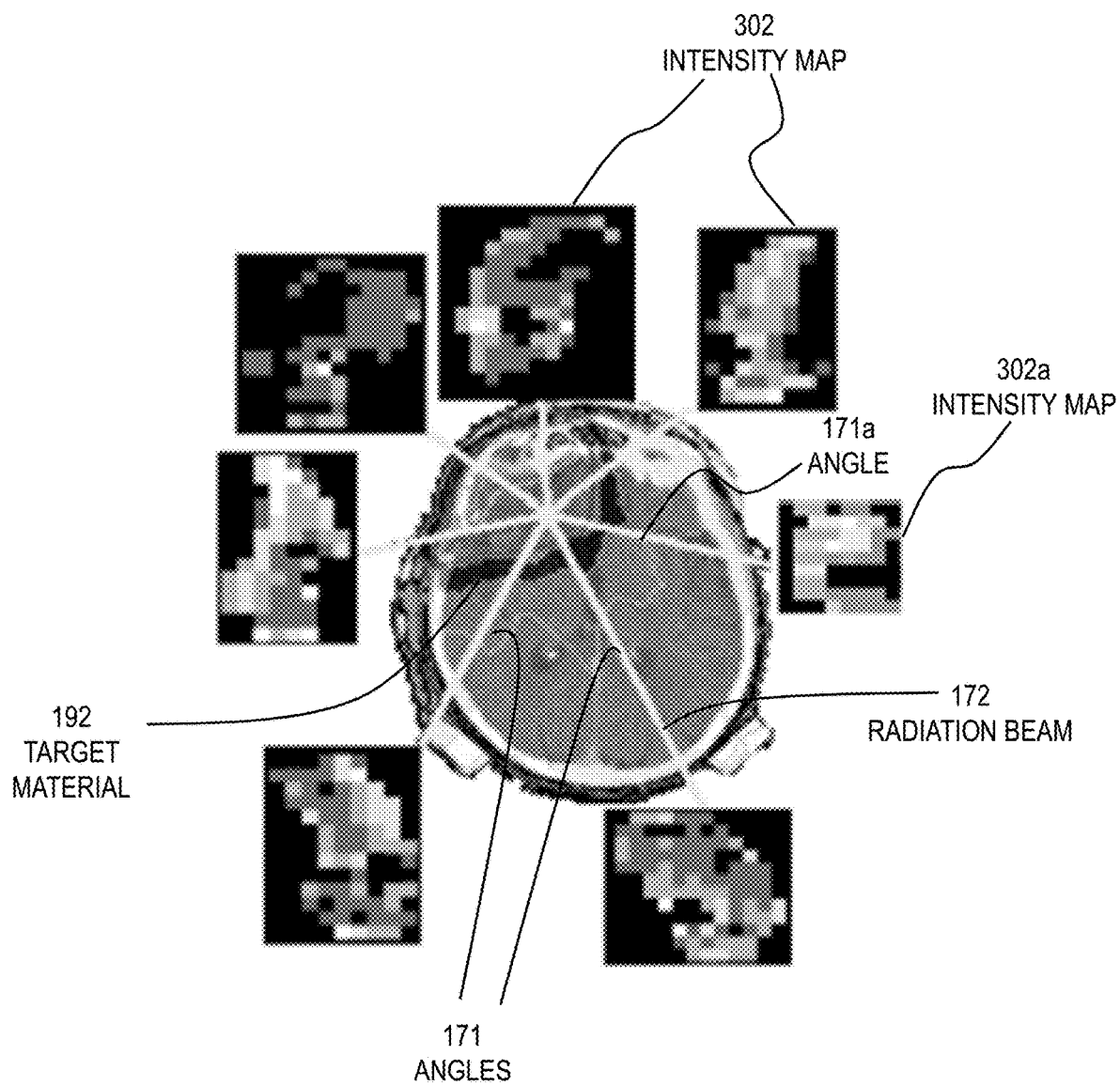

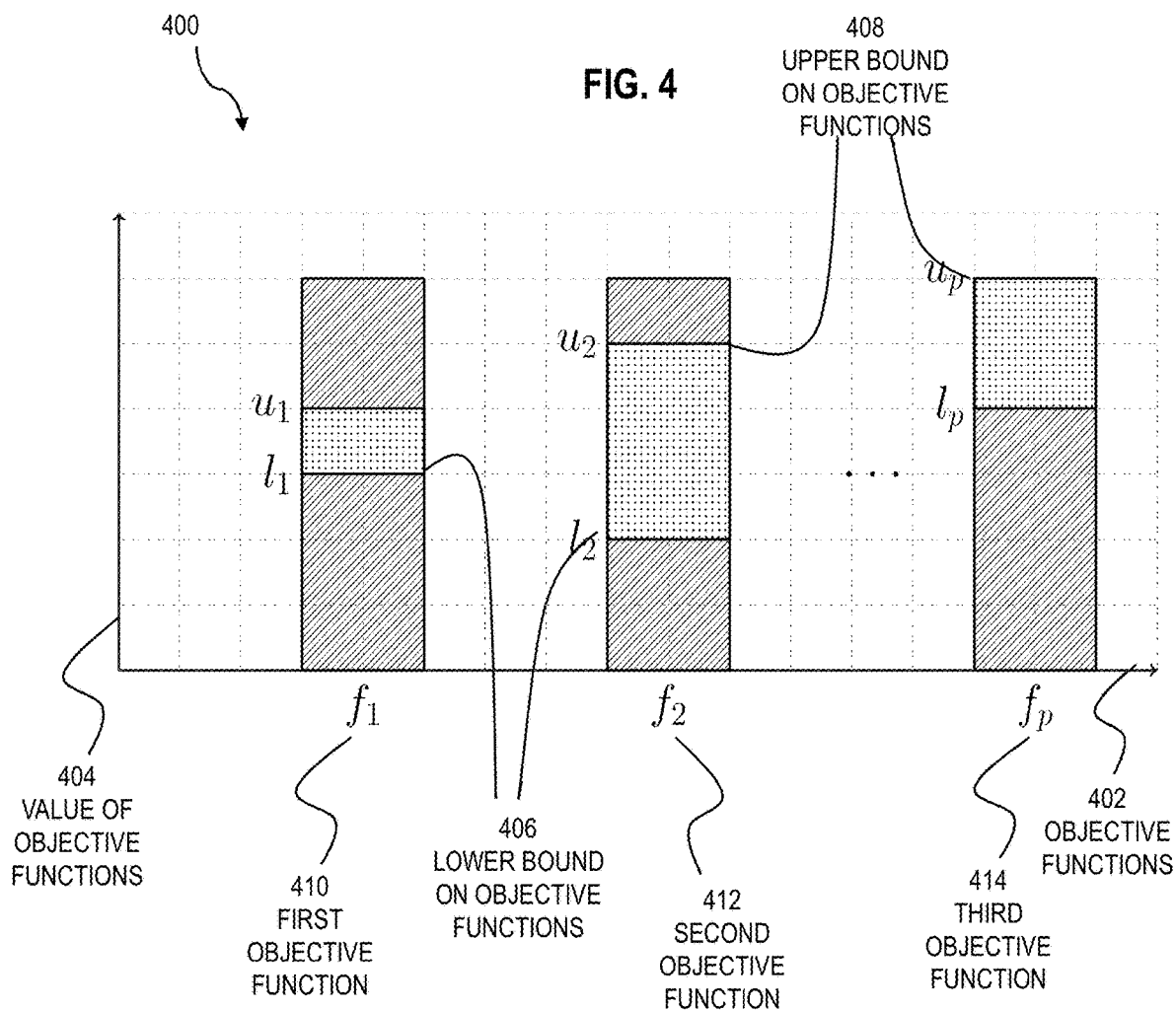

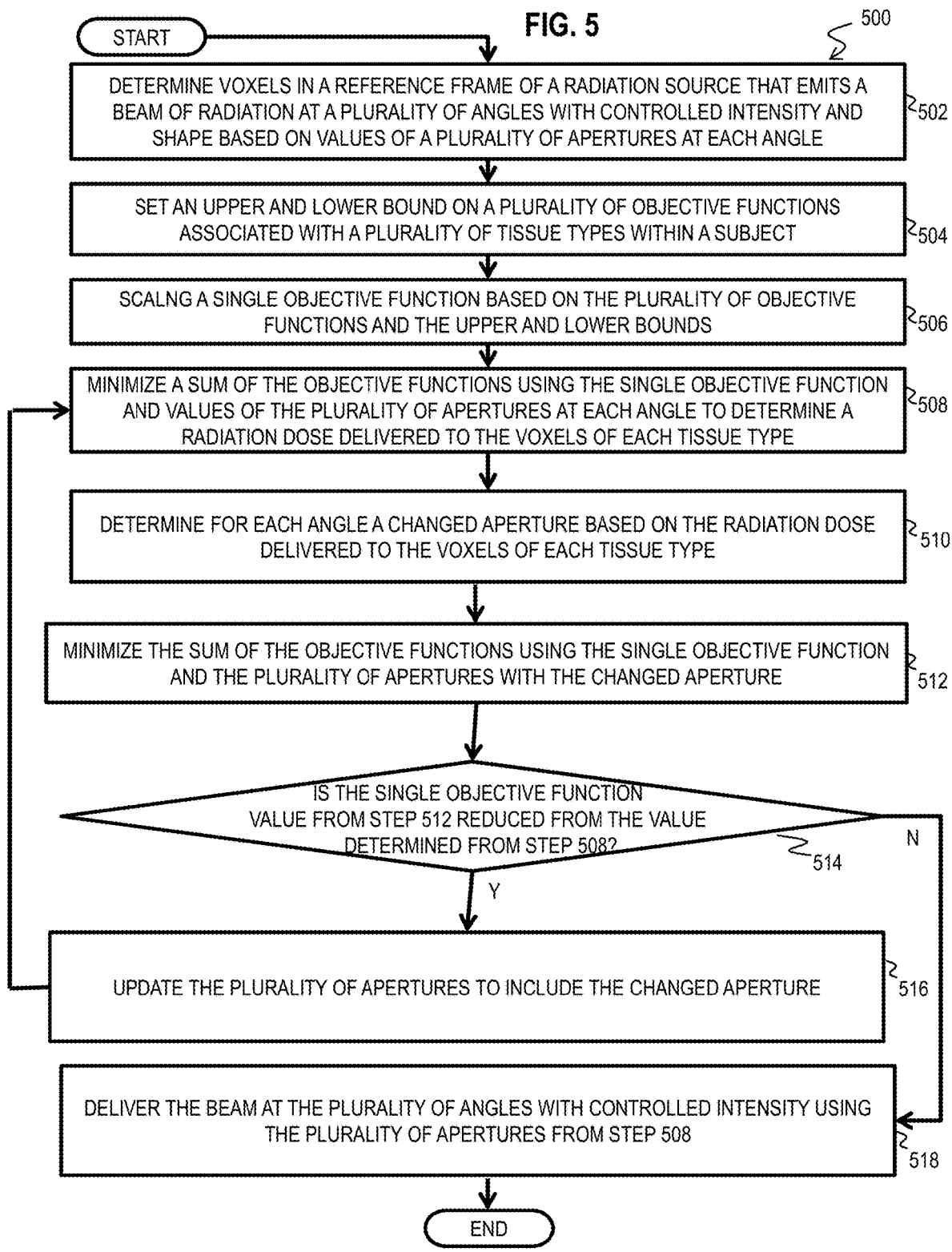

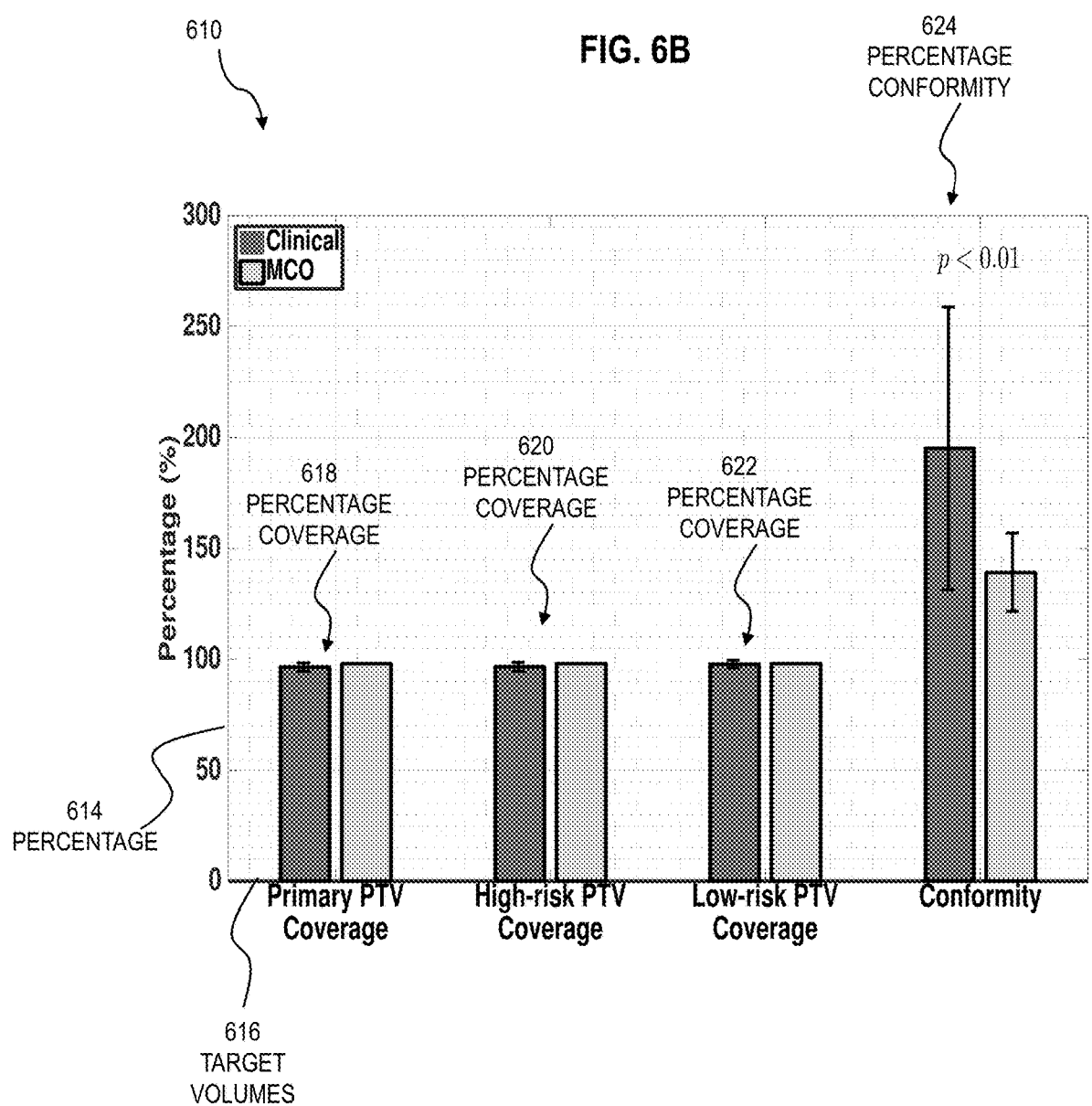

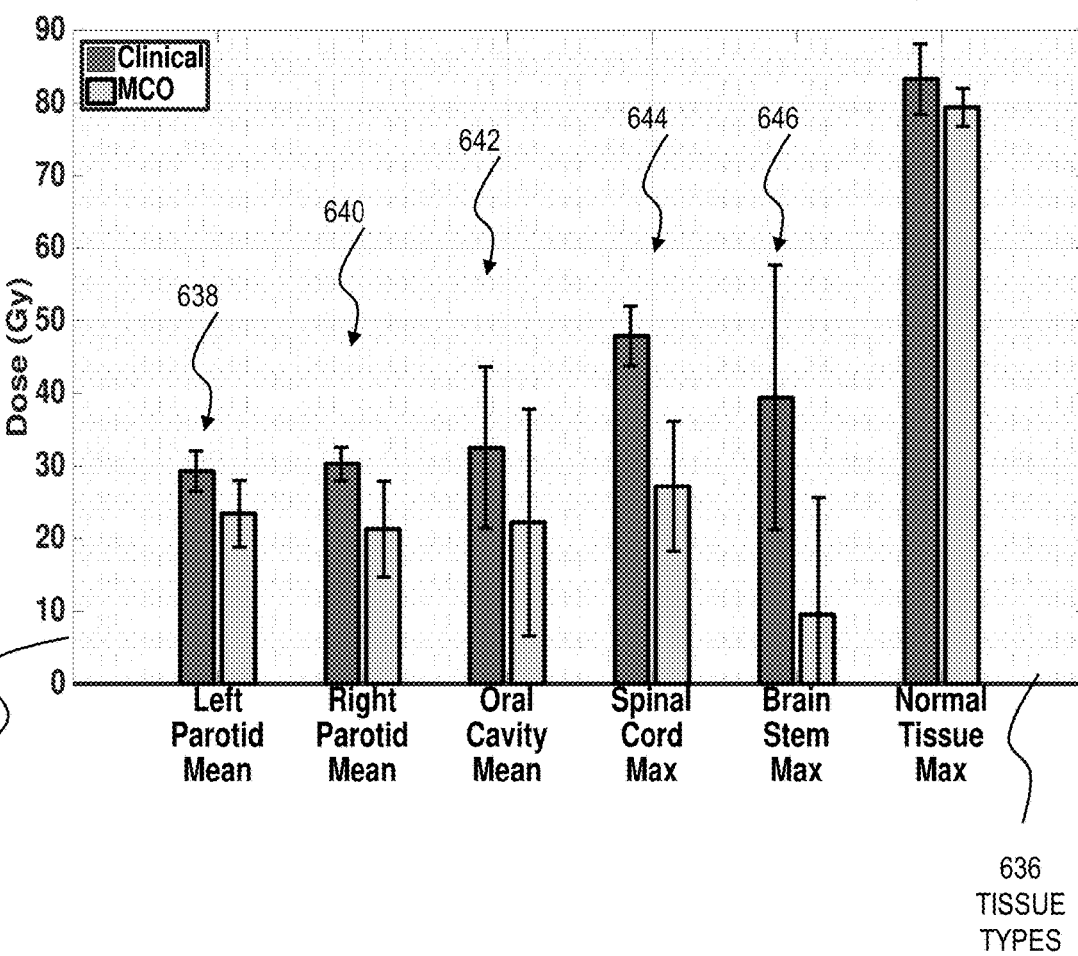

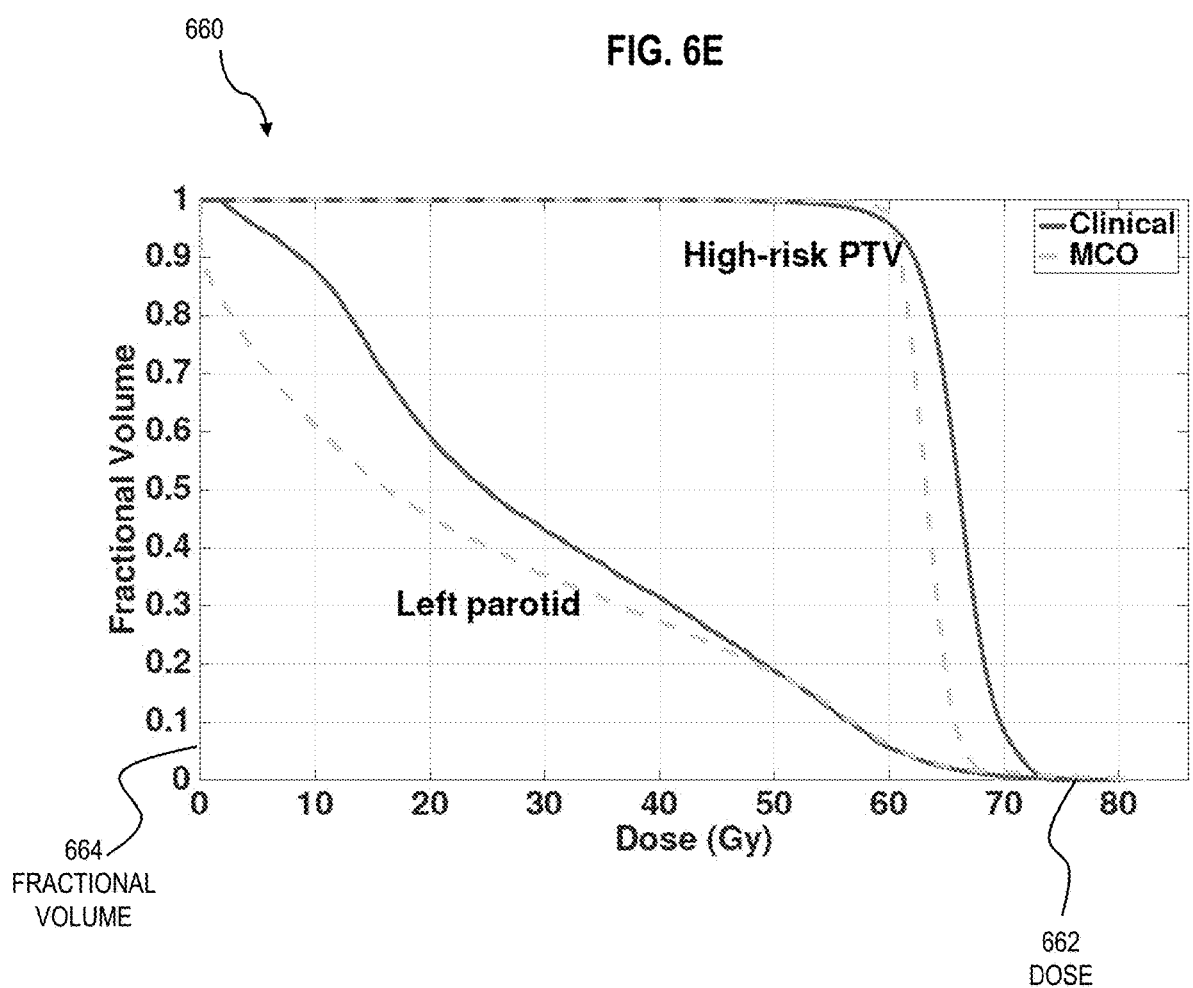

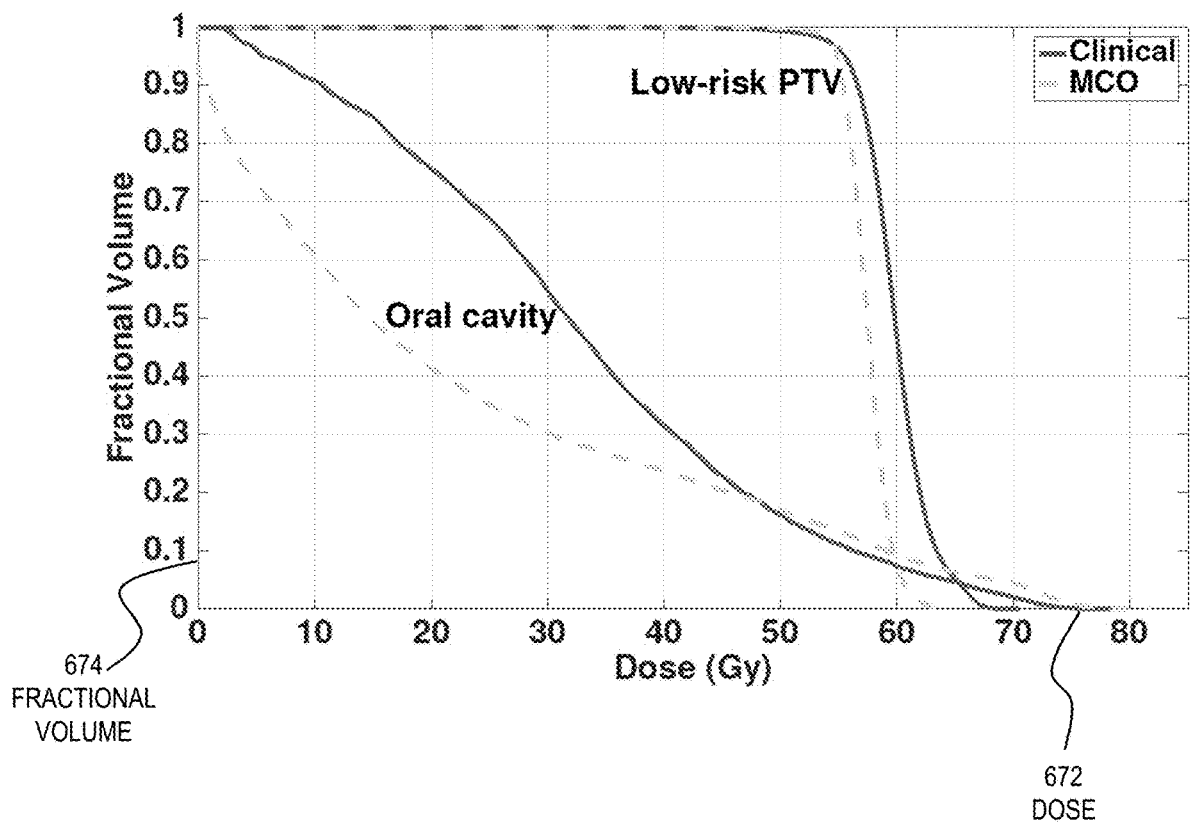

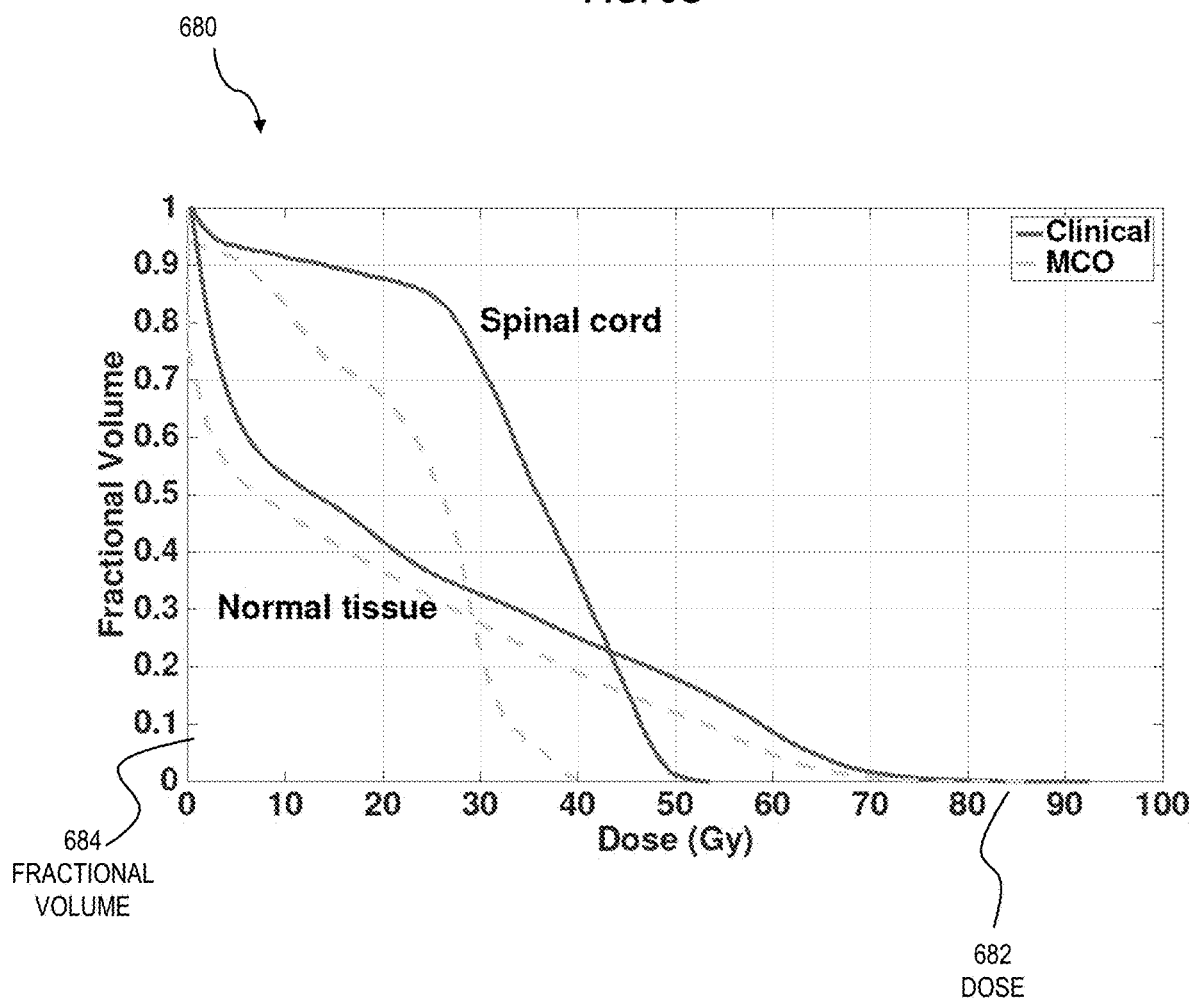

SYSTEM AND METHOD FOR OPTIMIZING A TREATMENT PLAN FOR IRRADIATION THERAPY USING MULTI-CRITERIA OPTIMIZATION (MCO)

CROSS-REFERENCE TO RELATED APPLICATIONS

This application claims benefit of Provisional Application No. 62/301,106, filed Feb. 29, 2016, under 35 U.S.C. § 119(e), the entire contents of which are hereby incorporated by reference as if fully set forth herein.

BACKGROUND

Radiotherapy is a treatment for cancer patients involving the use of high-energy radiation. When high-energy radiation is delivered to a subject, it kills cells in the body. Although the high-energy radiation kills tumor cells in the subject's body, it may also kill normal tissue cells and tissue cells of an organ-at-risk (OAR) that surround the tumor. Thus, the goal of conventional radiotherapy is to deliver a sufficient radiation dose to the tumor to kill the tumor cells while minimizing the radiation dose delivered to the normal tissue cells and OAR tissue cells that surround the tumor.

SUMMARY

It is here recognized that conventional multi-criteria optimization (MCO) methods for optimizing irradiation therapy are deficient, since they generate approximations of ideal treatment plans. Additionally, conventional MCO methods for optimizing irradiation therapy do not generate deliverable plans that can be used to directly control collimator apertures used to shape the beam during execution of the treatment plan. As a result, the treatment plan generated by the conventional MCO methods must be subsequently converted into a deliverable plan, which introduces quality degradation to the plan.

In a first set of embodiments, a method is provided for optimizing a treatment plan for irradiation therapy. The method includes determining a plurality of voxels in a reference frame of a radiation source that emits a beam of radiation at a plurality of angles with controlled intensity and beam cross sectional shape based on values of a plurality of apertures at each angle. The method further includes setting an upper and lower bound on a plurality of objective functions that are each associated with a plurality of tissue types within a subject. The method further includes defining a single objective function based on the plurality of objective functions, the upper and lower bound for each objective function and the plurality of apertures. The method further includes determining a radiation dose delivered to the voxels of each tissue type based on minimizing the single objective function using an initial set of one or more apertures at each angle. The method further includes delivering the beam of radiation with controlled intensity and beam cross sectional shape at each angle using the plurality of apertures.

In some embodiments of the first set, the method further includes determining for at least one angle a changed aperture based on the radiation dose delivered to the voxels at each tissue type. In some embodiments of the first set, the method further includes minimizing the single objective function using the plurality of apertures with the changed aperture such that the value of the single objective function is reduced from the value using the plurality of apertures without the changed aperture. In some embodiments of the first set, the delivering the beam of radiation with controlled intensity and beam cross sectional shape at each angle using the plurality of apertures includes delivering the beam of radiation with controlled intensity and beam cross sectional shape at each angle using the plurality of apertures with the changed aperture.

In a second set of embodiments, a computer-readable medium carrying one or more sequences of instructions is provided, where execution of the one or more sequences of instructions by one or more processors causes the one or more processors to perform the step of determining a plurality of voxels in a reference frame of a radiation source that emits a beam of radiation at a plurality of angles with controlled intensity and beam cross sectional shape based on values of a plurality of apertures at each angle. Additionally, execution of the one or more sequences of instructions further causes the processor to perform the step of defining a single objective function based on a plurality of objective functions that are each associated with a plurality of tissue types within a subject, an upper and lower bound of the plurality of objective functions and the plurality of apertures. Additionally, execution of the one or more sequences of instructions further causes the processor to perform the step of determining a radiation dose delivered to the voxels of each tissue type based on minimizing the single objective function using an initial set of one or more of the apertures at each angle. Additionally, execution of the one or more sequences of instructions further causes the processor to perform the step of delivering the beam of radiation with controlled intensity and beam cross sectional shape at each angle using the plurality of apertures.

In some embodiments of the second set, execution of the one or more sequences of instructions further causes the processor to perform the step of determining for at least one angle a changed aperture based on the radiation dose delivered to the voxels at each tissue type. Additionally, in some embodiments of the second set, execution of the one or more sequences of instructions further causes the processor to perform the step of minimizing the single objective function using the plurality of apertures with the changed aperture such that the value of the single objective function is reduced from the value using the plurality of apertures without the changed aperture. Additionally, in some embodiments of the second set, the step of delivering the beam of radiation with controlled intensity and beam cross sectional shape at each angle using the plurality of apertures includes delivering the beam of radiation with controlled intensity and beam cross sectional shape at each angle using the plurality of apertures with the changed aperture.

In a third set of embodiments, a system is provided for optimizing a treatment plan for irradiation therapy. The system includes a radiation source to emit a beam of radiation at a plurality of angles to each voxel of a plurality of voxels comprising a reference frame of the radiation source. The system further includes a plurality of apertures with values at each angle to control an intensity and cross sectional shape of the beam of radiation at each voxel in the reference frame. The system further includes a processor and a memory including one or more sequence of instructions. The memory and sequence of instructions is configured to cause the processor to define a single objective function based on a plurality of objective functions that are each associated with a plurality of tissue types within a subject, an upper and lower bound of the plurality of objective functions and the plurality of apertures. The memory and the sequence of instructions are configured to, with the processor, cause the processor to determine a radiation dose delivered to the voxels of each tissue type based on minimizing the single objective function using an initial set of one or more of the apertures at each angle. The memory and the sequence of instructions are configured to, with the processor, cause the processor to deliver the beam of radiation with controlled intensity and beam cross sectional shape at each angle using the plurality of apertures.

In some embodiments of the third set, the memory and the sequence of instructions are configured to, with the processor, cause the processor to determine for at least one angle a changed aperture based on the radiation dose delivered to the voxels of each tissue type. In some embodiments of the third set, the memory and the sequence of instructions are configured to, with the processor, cause the processor to minimize the single objective function using the plurality of apertures with the changed aperture such that the value of the single objective function is reduced from the value using the plurality of apertures without the changed aperture. In some embodiments of the third set, the delivery of the beam of radiation with controlled intensity and beam cross sectional shape at each angle using the plurality of apertures includes delivery of the beam of radiation with controlled intensity and beam cross sectional shape at each angle using the plurality of apertures with the changed aperture.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 1B is a block diagram that illustrates an example of scan elements in a 2D scan, such as one scanned image from a CT scanner;

FIG. 1C is a block diagram that illustrates an example of a plurality of voxels within a fixed frame of reference of the radiation source of FIG. 1A;

FIG. 3A is an image that illustrates an example of a plurality of intensity maps of the radiation beam of FIG. 1A at a plurality of angles, according to an embodiment;

FIG. 4 is a graph that illustrates an example of upper and lower bounds of a plurality of objective functions, according to an embodiment;

FIG. 5 is a flow diagram that illustrates an example of a method for optimizing a treatment plan for irradiation therapy, according to an embodiment;

FIG. 6B is a graph that illustrates an example of coverage and conformity of target volumes, according to an embodiment;

FIG. 6C is a graph that illustrates an example of mean and max dosages of organs-at-risk, critical organ and normal tissue, according to an embodiment;

FIG. 6E is a graph that illustrates an example of fractional volume versus dosage for a target volume and an organ-at-risk, according to an embodiment;

FIG. 6F is a graph that illustrates an example of fractional volume versus dosage for a target volume and an organ-at-risk, according to an embodiment;

FIG. 6G is a graph that illustrates an example of fractional volume versus dosage for a critical organ and normal tissue, according to an embodiment;

DETAILED DESCRIPTION

A method and apparatus are described for optimizing a treatment plan for irradiation therapy using multi-criteria optimization (MCO). In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5X to 2X, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of optimizing treatment plans for irradiation therapy of tumors of the head and neck. However, the invention is not limited to this context. In other embodiments, other targets of external radiation therapy in other regions of a human or non human subject are subjected to radiation.

1. Overview

Figure 1A:
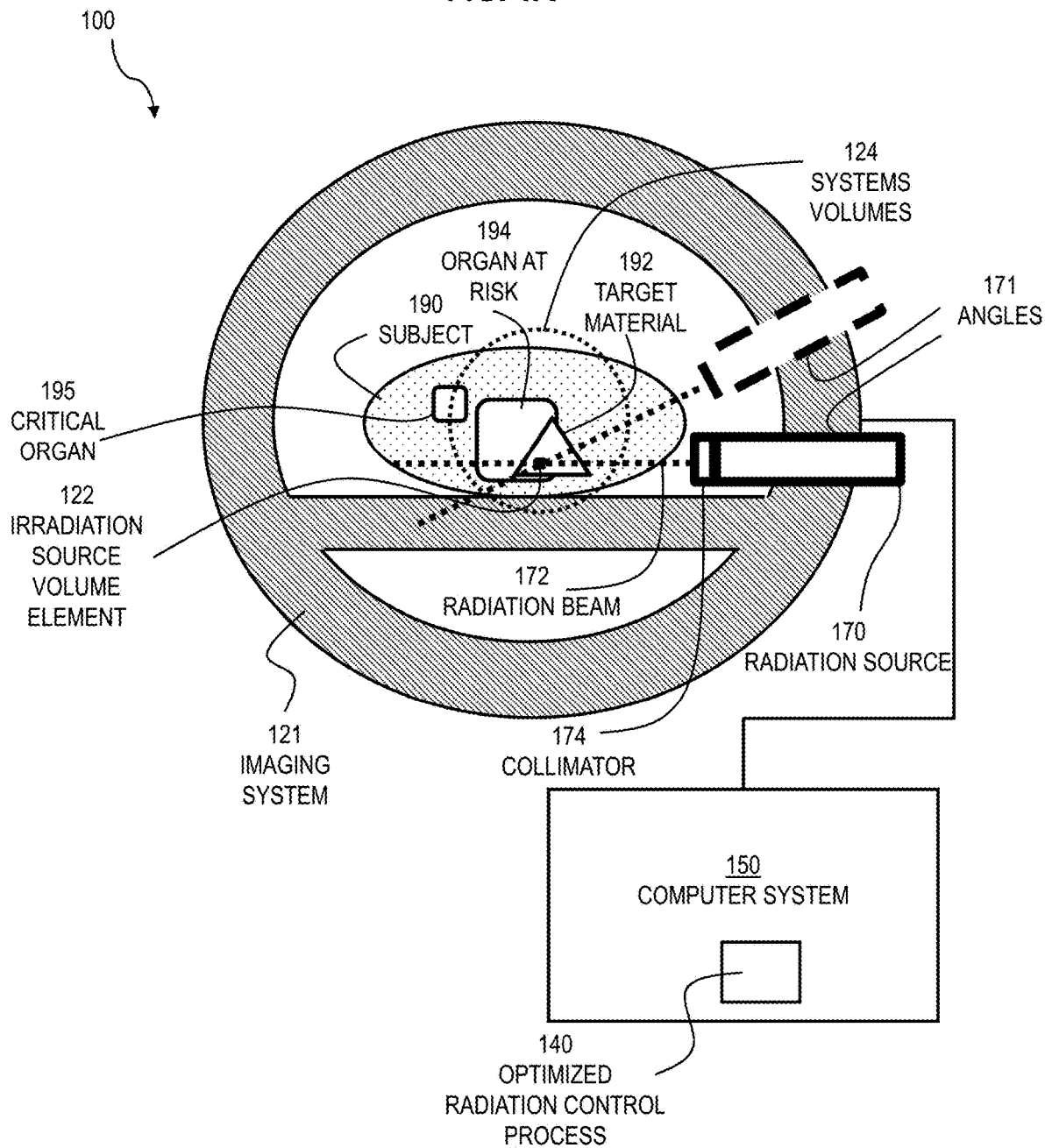
FIG. 1A is a block diagram that illustrates an example system for optimizing a treatment plan for irradiation therapy, according to an embodiment.

FIG. 1A is a block diagram that illustrates an example system 100 for optimizing a treatment plan for irradiation therapy, according to an embodiment. For purposes of illustration, a living subject 190 is depicted, but is not part of the system 100. Zero or more imaging systems 121 are provided, to image the subject 190 within a systems volume 124 that encompasses part of the subject 190. In some embodiments, the volume 124 may encompass the entire subject 190. A radiation source 170 is external to the volume 124 and directs radiation into the volume 124 of the subject 190. In an example embodiment, the imaging systems 121 obtain first measurements that relate to tissue type inside the volume 124. For example, the imaging system 121 is an X-ray Computed tomography (CT) scanner or a nuclear magnetic resonance imagery (MRI) scanner.

As illustrated in FIG. 1A, a target material 192 indicated by a triangle is positioned within the subject 190. In an example embodiment, the target material 192 includes tumor cells. Additionally, an organ-at-risk (OAR) 194 is positioned within the subject 190. Additionally, a critical organ 195 is positioned within the subject 190. The region of the volume 124 that is not occupied by the target material 192, the OAR 194 and the critical organ 195 is occupied by tissues in a category called normal tissue.

As illustrated in FIG. 1A, the system 100 includes a radiation therapy device including a collimator 174 and radiation source 170 that emits a beam 172 that penetrates the volume 124 over a plurality of volume elements or voxels 122 that are defined within a frame of reference of the radiation source 170. In some embodiments, the imaging systems 121 define the voxels 122 within the frame of reference of the radiation source 170. The radiation source 170 transmits the beam 172 through the collimator 174 to the voxels 122 within the volume 124. The beam 172 intensity and cross-sectional shape at each voxel 122 is dependent on apertures (not shown) of the collimator 174. Combining the effects of multiple beams (their intensities and cross-sectional shapes), the goal is to transmit a high dose to the target material 192 sufficient to damage or kill cells in that target material 192, and a low dose to the normal tissue, the critical organ 195 and the OAR 194.

During operation of the system 100, the radiation source 170 rotates through a plurality of angles 171 around the subject 190, so that the beam 172 is directed at the target material 192 from multiple angles 171. At each angle the beam intensity and aperture values of the collimator may change from those values at other angles, and multiple different intensity and aperture values may be used at the same angle. Although FIG. 1A depicts the radiation source 170 rotated through two angles 171, in one embodiment, the radiation source 170 is rotated through more than two angles 171 around the entire subject 190. At each angle 171, the radiation source 170 is stopped and irradiates the voxels 122 within the volume 124 with the beam 172 having a specific intensity and cross-sectional shape based on apertures of the collimator 174. In an example embodiment, if only one aperture is used for a series of angles 171, the radiation source 170 can continuously rotate around the subject 190 without stopping. The process may be repeated for multiple apertures and intensities. At some angles 171 of the radiation source 170, the beam 172 needs to pass through the OAR 194 to get to the target material 192. As illustrated in FIG. 1A, when the radiation source 170 rotates to an angle 171 on a left side of the target material 192, the beam 172 needs to pass through the OAR 194 to get to the target material 192. However, at other angles 171 of the radiation source 170, the beam 172 need not pass through the OAR 194 to get to the target material 192. As illustrated in FIG. 1A, when the radiation source 170 rotates to an angle 171 at a top side of the target material 192, the beam 172 need not pass through the OAR 194 to get to the target material 192.

Figure 7:
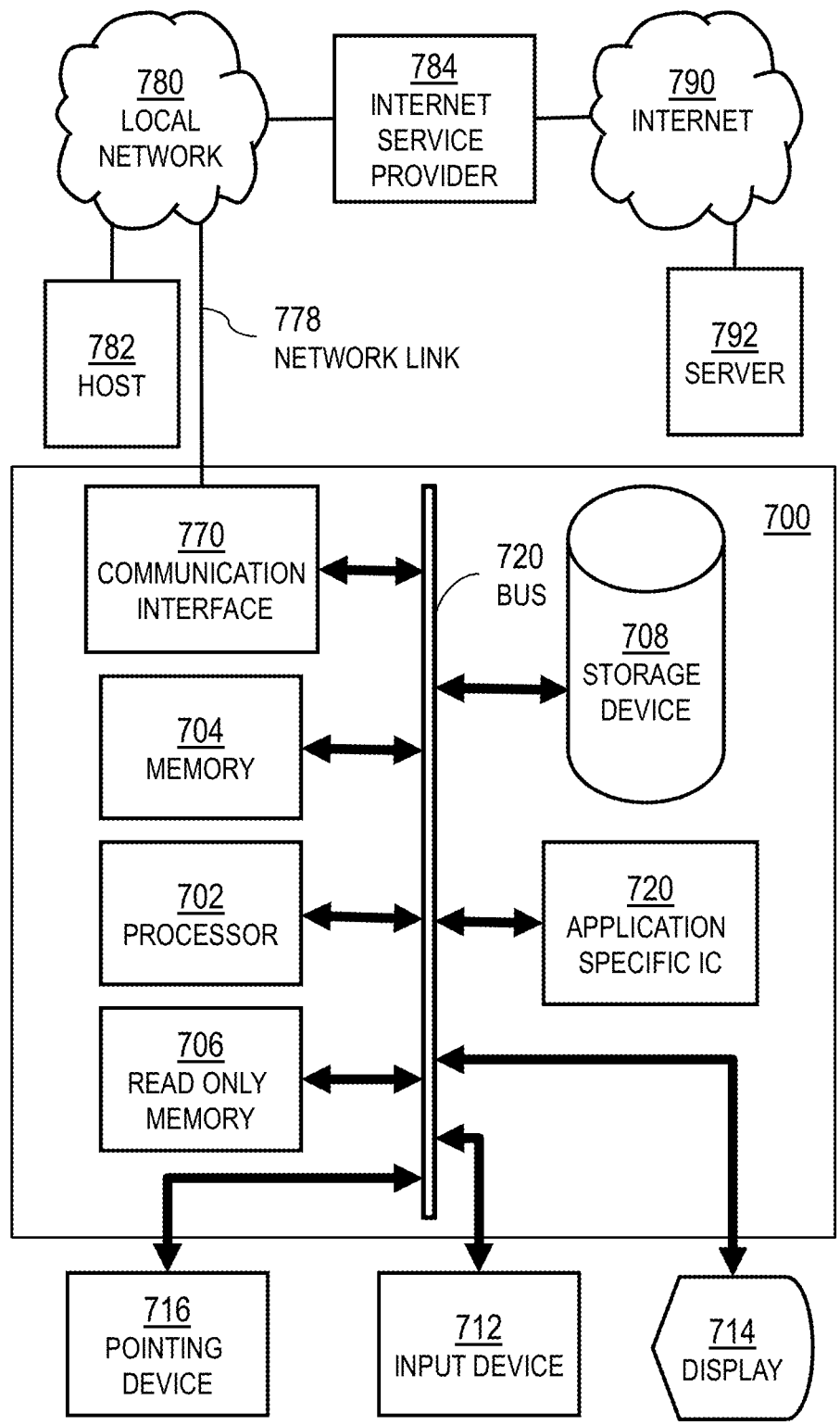
FIG. 7 is a block diagram that illustrates a computer system upon which an embodiment of the invention may be implemented.
Figure 8:
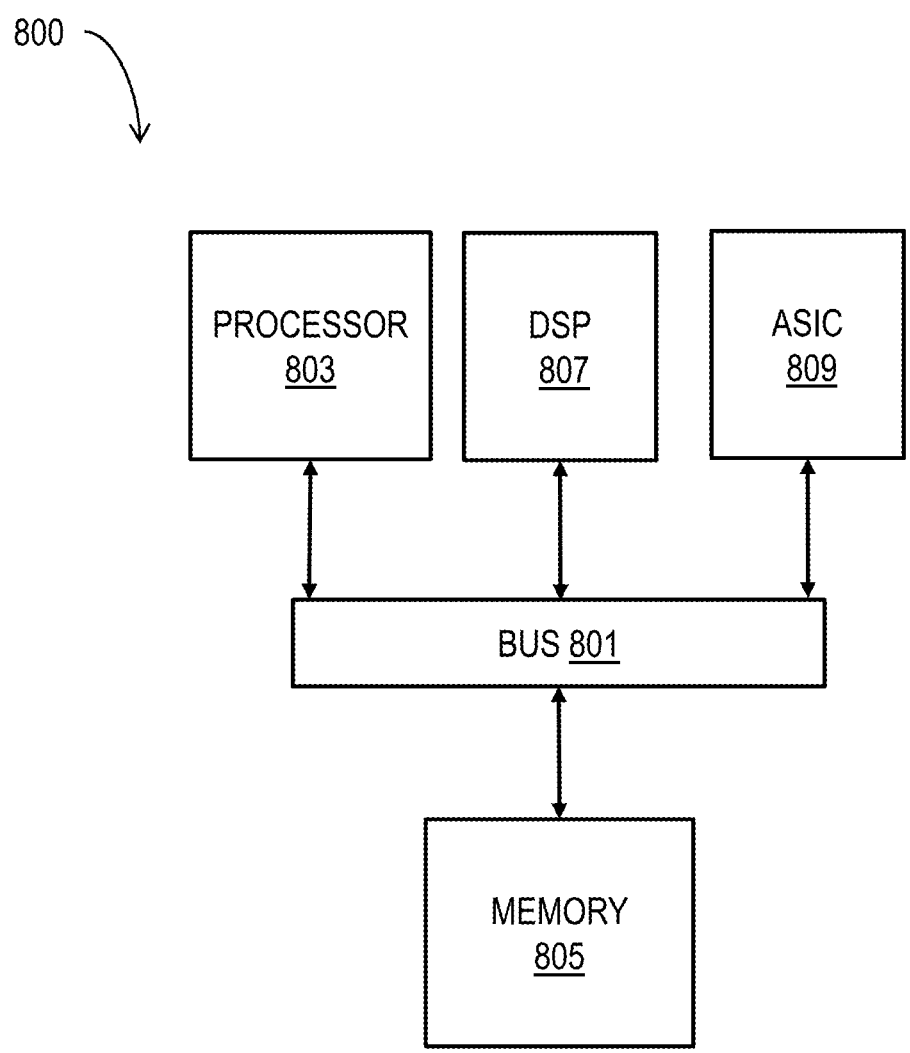
FIG. 8 is a block diagram that illustrates a chip set upon which an embodiment of the invention may be implemented.

As illustrated in FIG. 1A, a computer system 150 is provided to control the one or more imaging system 121, to collect imaging data from the one or more imaging system 121, and to determine a treatment plan including aperture values of the collimator 174 and intensity of the radiation source 170 at each angle 171. The computer system 150 includes an optimized radiation control process 140 to perform one or more steps of a method described below with reference to FIG. 5. In various embodiments, the computer system 150 comprises one or more general purpose computer systems, as depicted in FIG. 7 or one or more chip sets as depicted in FIG. 8, and instructions to cause the computer or chip set to perform one or more steps of a method described below with reference to FIG. 5.

FIG. 1B is a block diagram that illustrates scan elements in a 2D scan 110, such as one scanned image of the volume 124 from the imaging system 121, such as a CT scanner. The two dimensions of the scan 110 are represented by the x direction arrow 102 and the y direction arrow 104. The scan 110 consists of a two dimensional array of 2D scan elements (pixels) 112 each with an associated position. Typically, a 2D scan element position is given by a row number in the x direction and a column number in the y direction of a rectangular array of scan elements. A value at each scan element position represents a measured or computed intensity or amplitude that represents a physical property (e.g., X-ray absorption, or resonance frequency of an MRI scanner) at a corresponding position in at least a portion of the spatial arrangement of the living body. The measured property is called amplitude hereinafter and is treated as a scalar quantity. In some embodiments, two or more properties are measured together at a pixel location and multiple amplitudes are obtained that can be collected into a vector quantity, such as spectral amplitudes in MRSI. Although a particular number and arrangement of equal sized circular scan elements 112 are shown for purposes of illustration, in other embodiments, more elements in the same or different arrangement with the same or different sizes and shapes are included in a 2D scan.

FIG. 1C is a block diagram that illustrates the plurality of voxels 122 that are defined in the volume 124 within a fixed frame of reference of the radiation source 170 of FIG. 1A.

The fixed frame of reference of the radiation source 170 is defined based on the x-direction 102, y-direction 104 and z-direction 106. Thus, in an example embodiment, a particular voxel 122 within the volume 124 in the frame of reference of the radiation source 170 is assigned a unique x-value, y-value and z-value. As previously discussed, some of the voxels 122 are occupied by target material 192, some of the voxels 122 are occupied by OAR material 194, some of the voxels 122 are occupied by critical organ material 195 and the remaining voxels 122 in the volume 124 are occupied by normal tissue material. The computer system 150 determines aperture values of the collimator 174 at each angle 171 which determine the respective intensity of the beam 172 at each voxel 122. Although a particular number and arrangement of equal voxel 122 are shown for purposes of illustration, in other embodiments, more voxels 122 in the same or different arrangement with the same or different sizes and shapes are included in the frame of reference of the radiation source 170. In an example embodiment, the voxel 122 has a length in a range of 3-5 millimeters, a width in a range of 3-5 millimeters and a depth in a range of 2-3 millimeters.

Figure 2A:
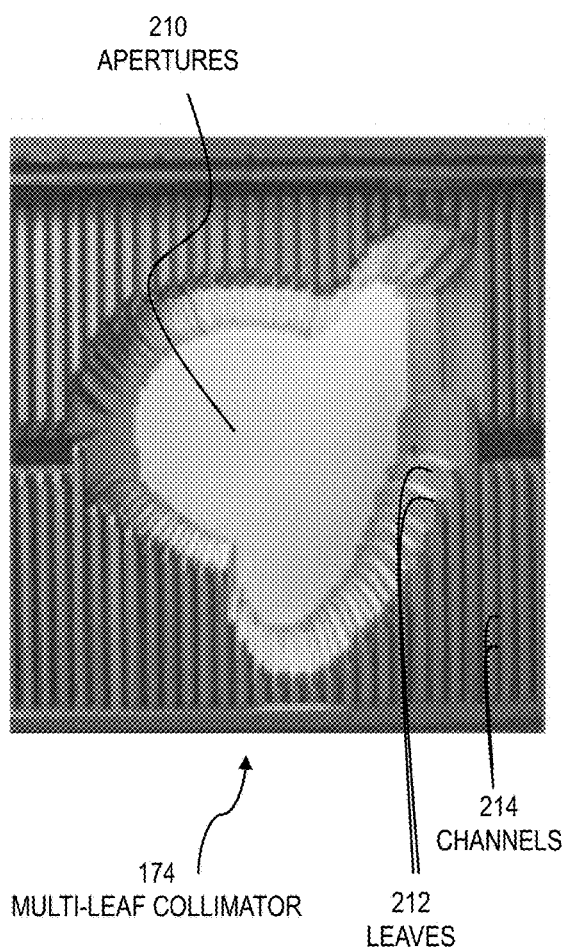
FIG. 2A is an image that illustrates an example of a multi-leaf collimator (MLC) used in the system of FIG. 1, according to an embodiment.
Figure 2B:
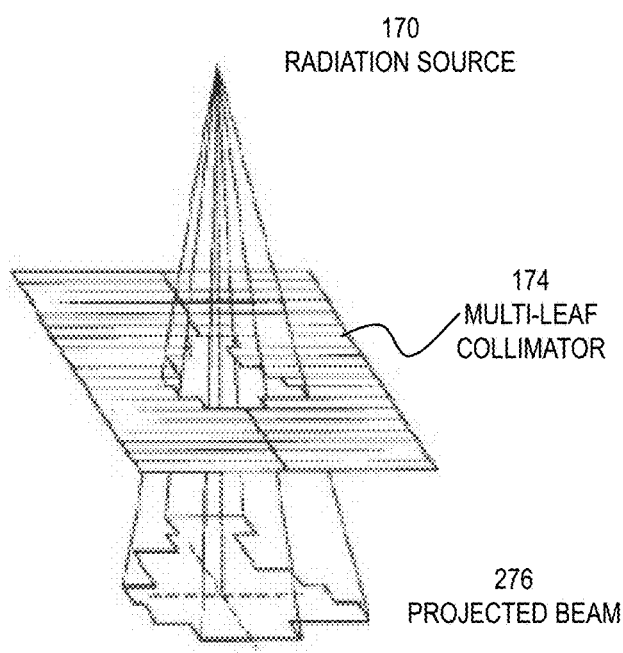
FIG. 2B is an image that illustrates an example of a projected beam from the radiation source that is shaped by the collimator of FIG. 1A, according to an embodiment.

FIG. 2A is an image that illustrates an example of a multi-leaf collimator (MLC) used as collimator 174 in the system of FIG. 1, according to an embodiment. The MLC 174 is positioned between the radiation source 170 and the subject 190 at each angle 171. In an embodiment, the MLC 174 is coupled to the radiation source 170 and rotates through each angle 171 with the radiation source 170. A surface area of the MLC 174 is divided into a plurality of apertures 210, which are formed by selectively moving metal leaves 212 within channels 214. In an embodiment, the value of each area element (such as a square area element of length and width equal to the channel width) within each aperture within the plurality of apertures 210 is either 0 (closed) or 1 (open). In the embodiment, a value of 0 corresponds to the area element of the aperture being a closed space occupied by metal leaves 212 whereas a value of 1 corresponds to the area element of the aperture being an open space that is not occupied by metal leaves 212. FIG. 2B is an image that illustrates an example of a projected beam 276 from the radiation source 170 that is shaped by the aperture area element values of the collimator 174 of FIG. 1A, according to an embodiment. Depending on the values of the apertures 210 within the collimator 174, the radiation beam 172 of FIG. 1A is selectively transmitted or blocked at each aperture, resulting in the projected beam 276 taking a specific cross-sectional shape and penetrating the voxels 122 within the volume 124. In an embodiment, the values of the apertures 210 are adjusted for each angle 171 such that a cross-section of the radiation beam 172 is selectively shaped at each angle 171 and consequently irradiates the voxels 122 of the volume 124 with a selective cross-sectional shape at each angle 171. For each angle 171 of index i, a set of apertures 210 of index k is represented by $K_i$, where each aperture of index k in the set $K_i$ has one or more open area elements or aperture values that correspond to beamlets. In an example embodiment, if the surface area of the MLC 174 is divided into 100 apertures, $K_1$ is a set of apertures at a first angle 171 of index i=1 that may include apertures #1, 37 and 59 of the 100 apertures, whereas $K_2$ is a set of apertures at a second angle 171 of index i=2 that may include apertures #2, 38, 61 of the 100 apertures. In various embodiments, multiple apertures are used at each angle, each aperture used with a corresponding constant or variable radiation source intensity. The net effect is a variable intensity beam directed to the subject at each angle. A beamlet is the part of each beam at each angle that goes through a single aperture area element, with the net intensity of the several apertures and radiation source intensities used at that angle.

FIG. 3A is an image that illustrates a plurality of intensity maps 302 of the radiation beam 172 of FIG. 1A at a plurality of (7) angles 171, according to an embodiment. The radiation beam 172 penetrates the target material 192 from the plurality of angles 171. The intensity map 302 displays the intensity and cross-sectional shape of the beam 172 at each angle 171, where each area element of each aperture is a shade of gray that indicates a corresponding intensity due to the net effect of multiple apertures and radiation source intensities. The values of the intensity map 302 at each angle 171 are based on a product of the value of each aperture 210 area element (FIG. 2A) and an intensity of the beam 172 at each of several apertures 210.

Figure 3B:
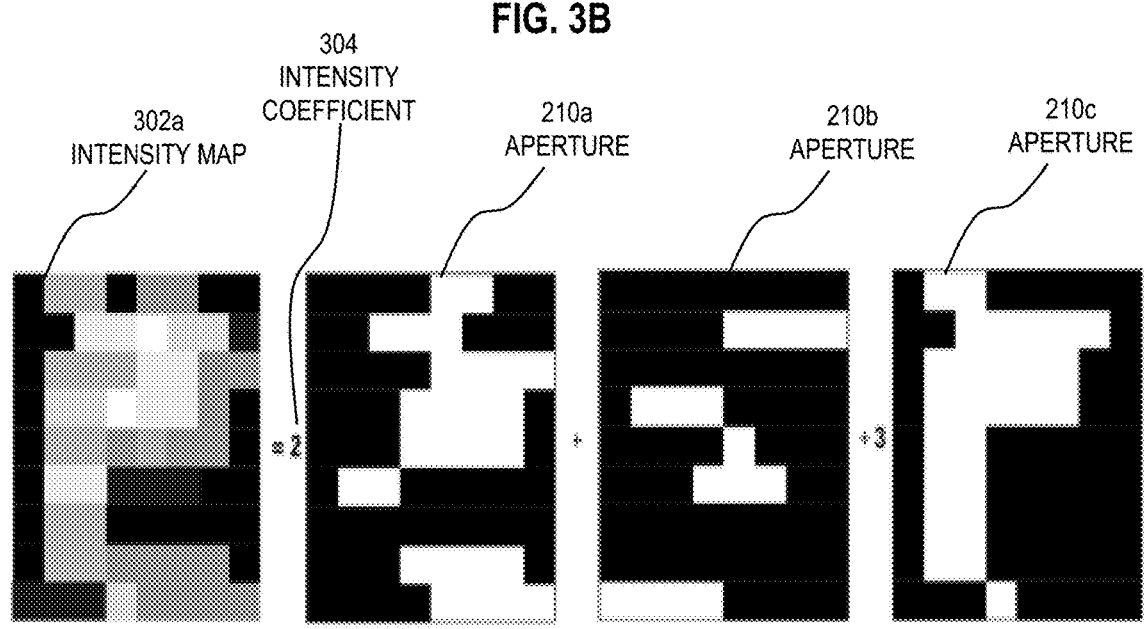
FIG. 3B is an image that illustrates an example of a plurality of apertures used to generate an intensity map of FIG. 3A at one of the plurality of angles, according to an embodiment.

FIG. 3B is an image that illustrates an example of a plurality of apertures 210a, 210b, 210c used to generate an intensity map 302a of FIG. 3A at one angle 171a of the plurality of angles, according to an embodiment. In some embodiments, the collimator 174 adjusts to each of the apertures 210a, 210b, 210c at different time periods and the beam 172 is directed at the angle 171a through each of the apertures 210a, 210b, 210c at an adjustable intensity at each time period. In one embodiment, the radiation source 170 remains fixed at the angle 171a over the different time periods. In other embodiments, the radiation source 170 rotates around the subject 190 between the time periods and stops at the angle 171a at each time period, such that the beam 172 is directed at the angle 171a through each of the different apertures 210a, 210b, 210c.

Figure 3C:
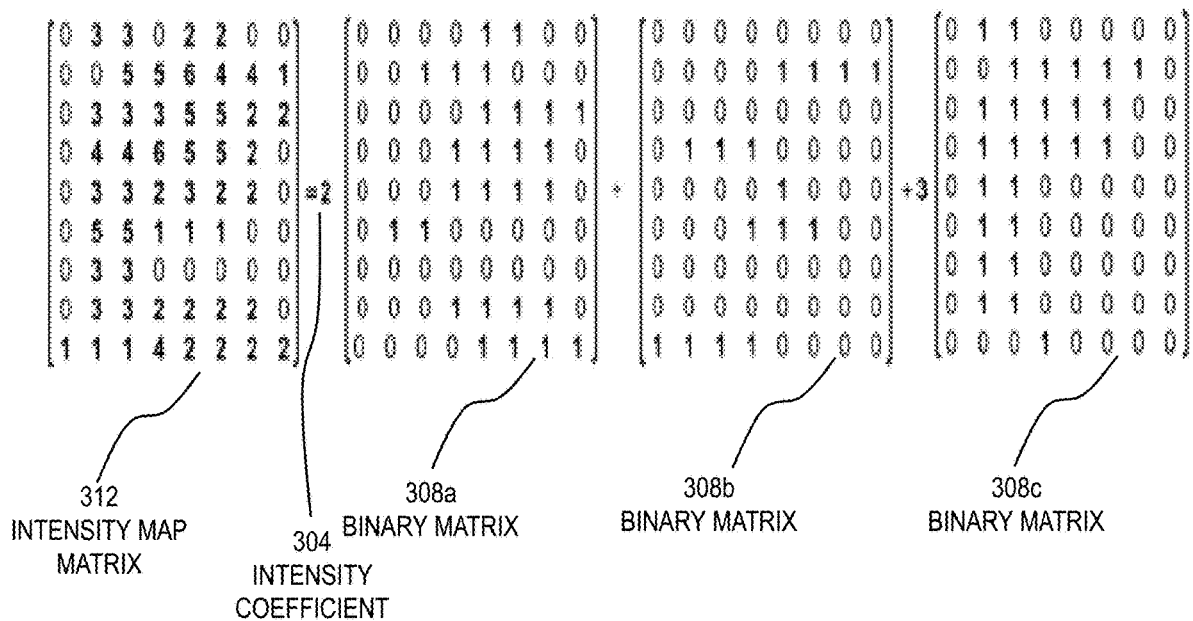
FIG. 3C illustrates an example of a plurality of binary matrices that represent the plurality of apertures of FIG. 3B, according to an embodiment.

Each aperture 210 includes an intensity coefficient 304 that indicates an amount of radiation or intensity of the beam 172 delivered through the respective aperture 210. FIG. 3C illustrates an example of a plurality of binary matrices 308a, 308b, 308c that represent the plurality of apertures 210a, 210b, 210c of FIG. 3B, according to an embodiment. Each binary matrix 308 includes elements with a value of 0 or 1 that correspond to respective area elements of the aperture 210, where 0 represents a closed area element and 1 represents an open area element of the aperture 210. Each binary matrix 308 is multiplied by the intensity coefficient 304 or amount of radiation delivered through the respective aperture 310. An intensity map matrix 312 is generated based on a sum of each binary matrix 308 multiplied by its respective intensity coefficient 304. Elements of the intensity map matrix 312 indicate a corresponding intensity due to the net effect of the multiple apertures 210 and radiation source intensities 304. In some embodiments, the greyscale intensity of the intensity map 302a is generated based on values of the elements of the intensity map matrix 312.

FIG. 4 is a graph 400 that illustrates an example of upper and lower bounds of a plurality of objective functions 410, 412, 414, according to an embodiment. These upper and lower bounds are used to scale the various objective functions so that they can be summed to produce a single objective function that can be minimized using standard techniques. In one embodiment, each objective function 410, 412, 414 is associated with a respective tissue type within the subject 190 among the target material 192, the OAR 194 material, the critical organ 195 material and the normal tissue material. In an example embodiment, the first objective function 410 is associated with the target material 192, the second objective function 412 is associated with the OAR 194 material and the third objective function 414 is associated with the critical organ 195 material. Although the graph 400 depicts three objective functions, the system 100 is not limited to three objective functions and can include less or more than three objective functions, where each objective function is associated with a respective tissue type of the subject 190.

As shown in the graph 400 of FIG. 4, the horizontal axis 402 is the different objective functions. The vertical axis 404 is the value of the objective functions. For each objective function 410, 412, 414, a lower bound 406 is depicted and an upper bound 408 is depicted. In an example embodiment, the lower bounds 406 and the upper bounds 408 for each objective function 410, 412, 414 are provided by a user of the system 100 and manually entered into the computer system 150. Although FIG. 4 depicts the upper and lower bounds 408, 406 of the three objective functions 410, 412, 414, these upper and lower bounds are not shown to scale and thus the upper bound 408 of the third objective function 414 may be less than the upper bounds 408 of the first and second objective functions 410, 412, for example.

In one embodiment, the objective function 410 associated with the target material 192 is a maximum variation between a prescription radiation dose, $PD_t$, to the target material 192 and a radiation dose $z_l$ received at each voxel 122 (with index l) within the target material 192, expressed as:

$$\max_{l \varepsilon V_t} |z_l - PD_t| \tag{1a}$$

where $V_t$ represents the volume within the target material 192.

In another embodiment, the objective function 410 associated with the target material 192 is a minimum dose within the target material 192, expressed as:

$$\min_{l \varepsilon V_t} z_l \tag{1b}$$

where $z_l$ is the radiation dose received at each voxel 122 (with index l) within the target material 192 and $V_t$ represents the volume of the target material 192.

In one embodiment, the objective function 412 associated with the OAR 194 material is a mean radiation dose within the OAR 194, expressed as:

$$\frac{\sum_{l \varepsilon V_o} z_l}{|V_o|} \tag{2}$$

where $z_l$ is the radiation dose received at each voxel 122 (with index l) within the OAR 194, $V_o$ represents the volume within the OAR 194 and $|V_o|$ is the number of voxels 122 within the OAR 194.

In one embodiment, the objective function 414 associated with the critical organ 195 material is a maximum dose within the critical organ 195, expressed as:

$$\max_{l \varepsilon V_c} z_l \tag{3}$$

where $z_l$ is the radiation dose received at each voxel 122 (with index l) within the critical organ 195 and $V_c$ represents the volume of the critical organ 195.

In one embodiment, an objective function associated with the normal tissue material is a maximum dose within the normal tissue, expressed as:

$$\max_{l \varepsilon V_n} z_l \tag{4}$$

where $z_l$ is the radiation dose received at each voxel 122 (with index l) within the normal tissue and $V_n$ represents the volume of the normal tissue.

The radiation dose $z_l$ received at each voxel 122 (index l), which is used in equations (1)-(4), is a function with intensity w and deposition time D as variables and with a predetermined set of angles and apertures as constants. In an embodiment, the radiation dose $z_l$ received at each voxel 122 (index l) can be expressed as:

$$z_l = \sum_{i \varepsilon \theta} \sum_{k \varepsilon K_i} w_{ik} \left( \sum_{j \varepsilon A_k} D_{ijl} \right) \tag{5}$$

where i is an index of the angle 171; θ is the plurality of angles 171; k is the index of each aperture 210; $K_i$ is the set of apertures 210 at the $i^{th}$ angle; $w_{ik}$ is the intensity value of the beam 172 at the $k^{th}$ aperture of the $i^{th}$ angle 171; j is an index of the beamlet within the beam 172; $A_k$ is a set of exposed (non-blocked) beamlets in the $k^{th}$ aperture; and $D_{ijl}$ is the dose deposition based on an amount of time that the beamlet of index j impinges the voxel of index l at the angle of index i. The values of the apertures 210 are factored in equation (5) by $A_k$, since the values of the apertures 210 affect which beamlets of index j are exposed through each aperture of index k.

FIG. 5 is a flow diagram that illustrates an example of a method 500 for optimizing a treatment plan for irradiation therapy, according to an embodiment. For example, one or more of the steps of method 500 are applied by process 140 of computer system 150. Although the flow diagram of FIG. 5 is depicted as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

After starting, in step 502, the voxels 122 are defined for the subject 190 in the fixed reference frame for the radiation source 170 for which the radiation beam 172 cross-sectional shape and intensity can be controlled by aperture values of the collimator 174 at each angle 171. As depicted in FIG. 1C, the voxels 122 are defined by the three-dimensional axes 102, 104, 106 in the fixed reference frame of the radiation source 170. Additionally, the voxels 122 are positioned within the systems volume 124 that encompasses a portion of the subject 190, such that each voxel 122 is a respective volume element within the volume 124. Additionally, as previously discussed, the intensity and cross-sectional shape of the beam 172 at each angle 171 can be controlled by the computer system 150 adjusting one or more values of the one or more apertures of the collimator 174 at each angle 171.

In step 504, the upper bounds 408 and lower bounds 406 are set for each objective function 410, 412, 414 that is associated with a respective tissue type within the subject 190. In one embodiment, the upper bounds 408 and lower bounds 406 of the objective functions 410, 412, 414 are manually input to the computer system 150 by a user. In an example embodiment, where the first objective function 410 is associated with the target material 192 and expressed as equation (1a) or (1b), in step 504 the upper bound 408 and lower bound 406 for the value of equation (1a) or (1b) are set. In an example embodiment, where the second objective function 412 is associated with the OAR 194 material and expressed as equation (2), in step 504 the upper bound 408 and lower bound 406 for the value of equation (2) are set. In an example embodiment, where the third objective function 414 is associated with the critical organ 195 material and expressed as equation (3), in step 504 the upper bound 408 and lower bound 406 for the value of equation (3) are set. In an example embodiment, where the fourth objective function is associated with the normal tissue material and expressed as equation (4), in step 504 the upper bound 408 and lower bound 406 for the value of equation (4) are set.

In step 506, parameters are defined for each objective function 410, 412, 414, based on the upper bounds 408 and lower bounds 406 for the objective functions 410, 412, 414 that were set in step 504. The parameters are used to scale the separate objective functions so that they can be summed into a single objective function and attributed the correct relative weights. The single objective function can then be minimized using any standard techniques known in the art. In one embodiment, a first parameter $r_j$ for each objective function 410, 412, 414 is the upper bound 408 of the objective function of index j, that is expressed as:

$$r_j = u_j \text{ for } j=1 \ldots p \qquad (6)$$

where $u_j$ is the upper bound 408 of the objective function with index j. In another embodiment, a second parameter $w_j$ is a reciprocal of a difference between the upper bound 408 and lower bound 406 of the objective function of index j, expressed as:

$$w_j = \frac{1}{u_j - l_j} \qquad (7)$$

where $u_j$ is the upper bound 408 and $l_j$ is the lower bound 406 of the objective function with index j. However, the parameters are not limited to these specific parameters and can include any parameters that are based on the upper bound 408 and/or the lower bound 406 of each objective function.

In step 508, the single objective function, a sum of the properly scaled objective functions 410, 412, 414 from step 506, is minimized. The proper scaling is achieved using the parameters set in step 506. The single objective function includes initial values for the one or more apertures 210 at each angle 171. In an example embodiment, the single objective function includes initial intensity values $w_{ik}$ for the beam 172 at one or more apertures 210 at each angle 171. In one embodiment, the single objective function is expressed as:

$$\min_{x \in X} \left\{ \max_{j=1,\ldots,p} w_j(f_j(x) - r_j) + \rho \sum_{j=1}^{p} w_j(f_j(x) - r_j) \right\} \qquad (8)$$

where f is one of the several objective functions having a j index from 1 to p; $r_j$ is the first parameter set in step 506 for the objective function with j index; $w_j$ is the second parameter set in step 506 for the objective function with j index; and p is a small positive number such as 0.0001. In one embodiment, the radiation dose $z_l$, expressed in equation (5), is substituted into each of the objective functions expressed in equations (1)-(4). As previously discussed, the values of the apertures 210 are factored in equation (5) by $A_k$, since the exposed beamlets of index j at each aperture of index k are based on the values of the apertures 210 at each angle 171. Additionally, as previously discussed, equation (5) includes the intensity values $w_{ik}$ for the beam 172 at the apertures 210 for each angle 171. In one embodiment, initial values of the apertures 210 and initial intensity values $w_{ik}$ are selected at each angle 171, such that each objective function expressed in equations (1)-(4) incorporates the initial values of the one or more apertures 210 and initial intensity values $w_{ik}$ at each angle 171. In one embodiment, the initial values of the apertures 210 are selected, such that the projected beam 276 (FIG. 2B) corresponds to a projected volume of the target material 192 at each angle 171. In one embodiment, the initial intensity values $w_{ik}$ of the apertures 210 are selected, such that the intensity of the projected beam 276 (FIG. 2B) corresponds to the prescription radiation dose $PD_t$ delivered to the target material 192 at each angle 171. The minimization of equation (8) results in a minimum value of each objective function 410, 412, 414 as well as a resulting parameter $\pi_l$ associated with each voxel 122 of index l.

In some embodiments, in step 508, the single objective function, a sum of the properly scaled objective functions 410, 412, 414 from step 506, is minimized, subject to one or more constraints. In some embodiments, the constraint is that a minimum percentage of the target material 192 receives the prescription dose $PD_t$, expressed as:

$$\varsigma_s - \frac{1}{(1-\alpha_s)|V_t|} \sum_{l \in V_t} \max(\varsigma_s - z_l, 0) \geq PD_t \qquad (9a)$$

where $\xi_s$ is a free variable; $(1-\alpha_s)$ is the minimum percentage of the target material 192 that receives the prescription dose $PD_t$, $V_t$ is the volume of the target material 192; $z_l$ is the dose received at the voxel of index l and $|V_t|$ is the number of voxels within the target material 192.

In other embodiments, the constraint is that a maximum percentage of the OAR 194 material receives more than a dose $PD_o$, expressed as:

$$\varsigma_O + \frac{1}{(1-\alpha_O)|V_O|} \sum_{l \in V_O} \max(z_l - \varsigma_O, 0) \leq PD_O \qquad (9b)$$

where $\xi_o$ is a free variable; $(1-\alpha_o)$ is the maximum percentage of the OAR material 194 that receives the dose $PD_O$, $V_O$ is the volume of the OAR material 194; $z_l$ is the dose received at the voxel of index l and $|V_O|$ is the number of voxels within the OAR material 194.

In step 510, for one or more angles 171, one of the initial values of the apertures 210 selected in step 508 is replaced with a value based on the parameter $\pi_l$ associated with each voxel 122 of index l determined in step 508 or a new aperture value is added to the initial values of the apertures 210 based on the parameter $\pi_l$. If one of the initial values of the apertures 210 is replaced with a value, then $A_k$ in equation (5) is changed to incorporate this replaced aperture value. Similarly, if a new aperture value is added to the initial values of the apertures 210, then $A_k$ in equation (5) is changed to incorporate this new aperture value. For example, if the dose at a particular voxel is too high one or more apertures are changed to reduce the intensities of beamlets that impinge on that voxel or a new aperture is added to the set of apertures at that angle and the new aperture is open for the beamlets that impinge on the voxel that is too low but is closed for beamlets that impinge on a voxel that is too high. In either case, the change to an existing aperture or the addition of a new aperture, or both, is called a changed aperture hereinafter. In one embodiment, step 510 is performed for each angle 171.

In step 512, the single objective function, the sum of the properly scaled objective functions 410, 412, 414 is minimized. The proper scaling is achieved, using the parameters set in step 506. The single objective function includes the initial values of the apertures 210 and changed aperture from step 510. In an embodiment, the minimization of the sum of the objective functions 410, 412, 414 is performed using equation (8), which results in a minimum value for the sum of each objective function 410, 412, 414.

Figure 6A:
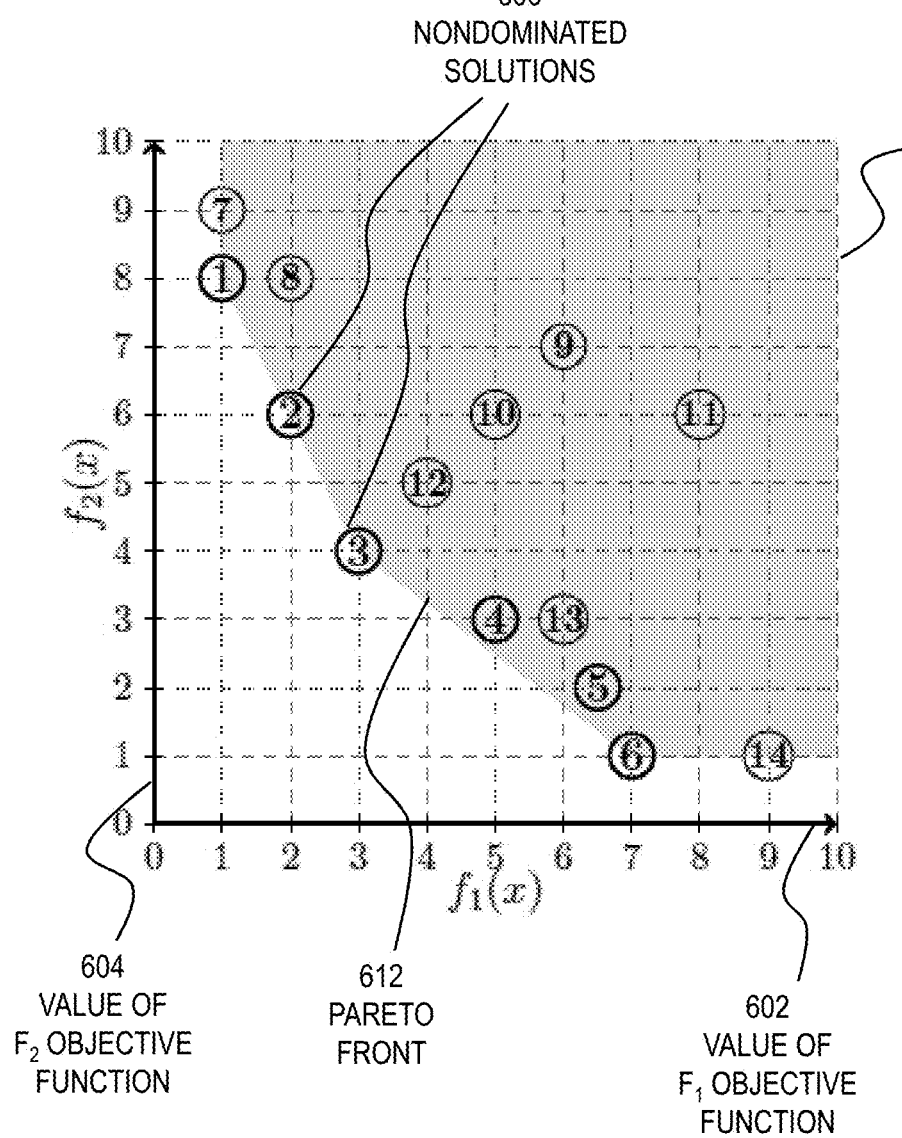
FIG. 6A is a graph that illustrates an example of multiple solutions to the optimizing of a treatment plan with two objective functions, according to an embodiment.

In step 514, the value of the single objective function from the minimizing of step 512 is compared with the value of the single objective function from the minimizing of step 508. A determination is made whether the value of the single objective function from the minimizing of step 512 is reduced from the value of the single objective function from the minimizing of step 508. FIG. 6A is a graph 600 that illustrates an example of multiple solutions to the minimizing of a single objective function based on two objective functions $f_1$, $f_2$, according to an embodiment. The horizontal axis 602 is a value of a first objective function $f_1$. The vertical axis 604 is a value of a second objective function $f_2$. The graph 600 shows a shaded region 608 that encompasses solutions to the minimizing of steps 508 and 512, where two objective functions $f_1$, $f_2$ are used. The circled numbers in the shaded region 608 correspond to computed minimum values of $f_1$ and $f_2$ according to the minimizing step. In an example embodiment, the minimizing of step 508 results in solution #9 and the minimizing of step 512 results in solution #2. In this example embodiment, the value of each objective function $f_1$, $f_2$ from the minimizing of step 512 (2 and 6, respectively) is reduced from the respective value of each objective function $f_1$, $f_2$ from the minimizing of step 508 (6 and 7, respectively). From equation (8), the value of the single objective function is based on values of the objective functions $f_1$ and $f_2$ and thus, the value of the single objective function from the minimizing of step 512 is reduced from the value of the single objective function from the minimizing of step 508.

In step 516, if the determination in step 514 is affirmative, the initial values of the apertures 210 are updated to include the changed aperture from step 510. As previously discussed, this step involves updating the exposed beamlets $A_k$ in equation (5), to incorporate the changed aperture value from step 510. The method 500 then proceeds to step 508 and uses these updated initial values of the apertures 210. The method 500 proceeds back to step 508, to perform another iteration of steps 508-514 to ensure that these updated initial values of the apertures 210 in step 516 achieve an optimal or nondominated solution. As shown in FIG. 6A, the shaded region 608 encompassing all solutions includes a pareto front 612 on which the optimal solutions or nondominated solutions 606 reside (solutions #1-6). These nondominated solutions 606 are considered optimal since no reduction in the value of the single objective function is possible, since no reduction in the value of an objective function $f_1$, $f_2$ is possible without increasing the value of the other objective function $f_1$, $f_2$. For example, moving from nondominated solution #2 to solution #12 involves a reduction in the value of $f_2$, but an increase in the value of $f_1$ and thus does not involve a reduction in the value of the single objective function. In another example, moving from nondominated solution #3 to solution #8 involves a reduction in the value of $f_1$ but an increase in the value of $f_2$ and thus similarly does not involves a reduction in the value of the single objective function.

In step 518, if the determination in step 514 is negative, then the value of the single objective function from the minimizing of step 512 has increased from the value of the single objective function from the minimizing of step 508. As a result, the values of the objective functions from the minimizing of step 508 is an optimal or nondominated solution 606. The values of the apertures 210 of the collimator 174 are adjusted at each angle 171 based on the initial values of the apertures 210 used in step 508, to deliver the beam 172 at the plurality of angles 171 with controlled intensity and cross-sectional shape. In another embodiment, the intensity of the beam 172 is adjusted at each angle 171 based on the initial intensity values $w_{ik}$ used in step 508, to deliver the beam 172 at the plurality of angles 171 with controlled intensity and cross-sectional shape.

In an example embodiment, during a first iteration of steps 508-514, the values of the objective functions move from solution #10 (minimizing step 508) to solution #12 (minimizing step 512) in FIG. 6A. During step 514, since the value of the single objective function was reduced from solution #10 to solution #12, the method proceeds to step 516 and another iteration of steps 508-514 is performed. In this example embodiment, during the second iteration of steps 508-514, the values of the objective functions move from solution #12 (minimizing step 508) to solution #3 (minimizing step 512) in FIG. 6A. Again, during step 514, since the value of the single objective function was reduced from solution #12 to solution #3, the method proceeds to step 516 and another iteration of steps 508-514 is performed. In this example embodiment, during a third iteration of steps 508-514, the values of the objective functions move from solution #3 (minimizing step 508) to a solution (#8, #13, etc) where a value of at least one objective function $f_1$, $f_2$ necessarily increases. During step 514, since the value of the single objective function was not reduced, the solution #3 (from minimizing step 508) is a nondominated solution 606 and thus the method proceeds to step 518 where the values of the apertures 210 of the collimator 174 are adjusted at each angle 171 based on the values of the apertures 210 used in step 508.

2. Example Embodiments

In some embodiments of the method 500, in step 510, the resulting parameter $\pi_i$ from step 508 is used as input to solve a pricing problem defined as:

$$\delta_i = \min_{y \in W_i} \sum_{j \in N_i} \left( \sum_{\substack{l \in V_s \\ s \in S}} -D_{ijl} \pi_l \right) y_j \qquad (10)$$

$$\delta = \min_{i \in \theta} \delta_i \qquad (11)$$

$$\hat{\imath} = \arg\min_{i \in \theta} \delta_i \qquad (12)$$

where y is the aperture 210 that is a variable in equation (10); $W_i$ is a set of all feasible apertures 210 at an angle of index i; $y_j$ is a binary value $\{0, 1\}$ and indicates whether the beamlet of index j is exposed or not in the aperture 210; $N_i$ is a set of all beamlets at the angle of index i. $\delta_i$ of equation (10) is solved for each angle i, by varying the aperture y among all feasible apertures $W_i$. $\delta$ of equation (11) is determined as the minimum value of $\delta_i$ among all angles of index i. The angle $\hat{i}$ of equation (12) is the angle of $\delta_i$ that satisfies equation (11).

In these embodiments of the method 500, step 512 is omitted and step 514 involves determining whether $\delta$ of equation (11) is <0. If $\delta$ is <0, the method 500 moves to step 516 and the aperture y associated with the beam angle $\hat{i}$ in equation (12) is added to the plurality of apertures. If $\delta$ is <0, the method 500 moves to step 518.

Figure 9A:
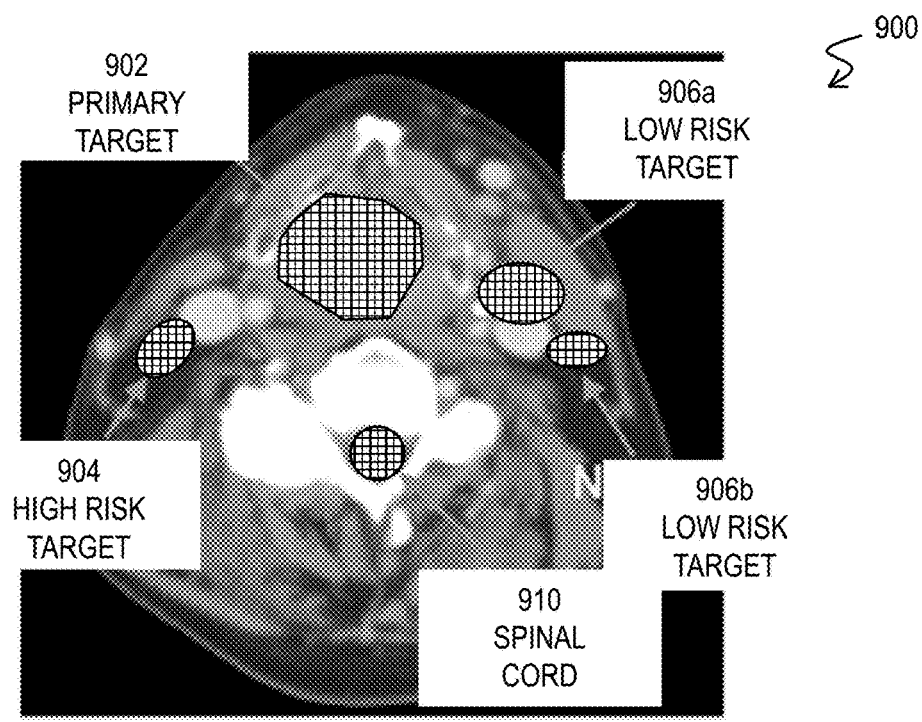
FIG. 9A is an image that illustrates an example of an organ-at-risk volume and multiple target volumes in the head and neck of a subject, according to an embodiment.
Figure 9B:
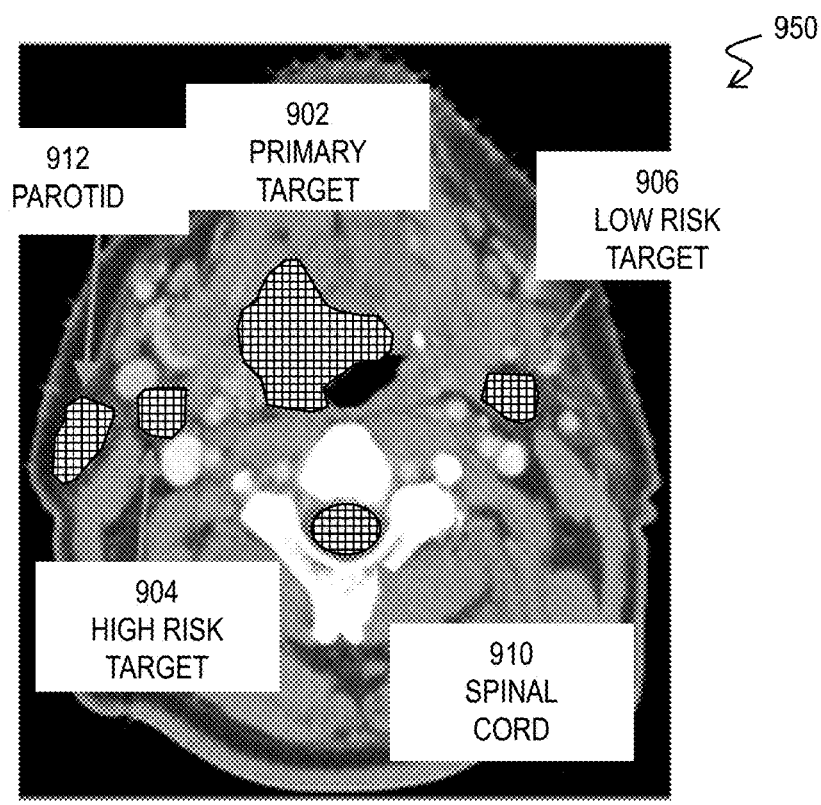
FIG. 9B is an image that illustrates an example of an organ-at-risk volume and multiple target volumes in the head and neck of a subject, according to an embodiment.

In some embodiments, step 504 is performed for more than one volume of target material 192, such that the upper bound and lower bound of the objective function 410 associated with equation (1a) or equation (1b) is set for each volume of target material 192. In an example embodiment, step 504 is performed for one or more of a primary target 902 volume, a high-risk target 904 volume and a low-risk target 906a, 906b volume. FIG. 9A is an image 900 that illustrates an example of the critical organ (e.g. spinal cord 910) volume and multiple target 902, 904, 906 volumes in the head and neck of a subject, according to an embodiment. FIG. 9B is an image 950 that illustrates an example of an organ-at-risk (e.g. parotid 912) volume and multiple target 902, 904, 906 volumes in a head and neck of a subject, according to an embodiment. In this example embodiment, the method is used to treat locally advanced head and neck cancer cases, such as oropharynx, nasopharynx, larynx and hypopharynx. In this example embodiment, the respective prescription dose $PD_t$ in equation (1a) for the primary target 902 volume, high-risk target 904 volume and low-risk target 906 volume is 70 Gray (Gy), 59.4 Gy and 54 Gy. In an example embodiment, the upper bound and lower bound for the dose $PD_t$ of the primary target 902 volume is 77 Gy and 70 Gy, respectively. In an example embodiment, the upper bound and lower bound for the dose $PD_t$ of the high-risk target 904 volume is 65 Gy and 59.4 Gy, respectively. In an example embodiment, the upper bound and lower bound for the dose $PD_t$ of the low-risk target 906 volume is 59.4 Gy and 54 Gy, respectively.

In some embodiments, step 504 is also performed for more than one OAR 194, such that the upper bound and lower bound of the objective function 412 associated with equation (2) is set for each OAR 194. In an example embodiment, step 504 is performed for one or more of a left parotid 912, a right parotid and an oral cavity. In this example embodiment, the respective upper and lower bounds of the mean dose expressed in equation (2) for the left and right parotids 912 is 20 Gy and 26 Gy, respectively. In this example embodiment, the upper and lower bounds of the mean dose expressed in equation (2) for the oral cavity is 35 Gy and 40 Gy, respectively.

In some embodiments, step 504 is also performed for more than one critical organ 195, such that the upper bound and lower bound of the objective function 414 associated with equation (3) is set for each critical organ 195. In an example embodiment, step 504 is performed for a spinal cord 910 and/or a brain stem. In this example embodiment, the upper and lower bounds of the maximum dose expressed in equation (3) for the spinal cord 910 is 40 Gy and 45 Gy, respectively. In this example embodiment, the upper and lower bounds of the maximum dose expressed in equation (3) for the brain stem is 50 Gy and 54 Gy, respectively.

In some embodiments, step 504 is also performed for normal tissue, such that the upper bound and lower bound of the objective function 414 associated with equation (4) is set for the normal tissue. In an example embodiment, the upper and lower bounds of the maximum dose expressed in equation (4) for the normal tissue is 70 Gy and 80 Gy, respectively.

In other embodiments, step 508 is performed by setting the minimum percentage $\alpha_s$ in the constraint of equation (9a) at 95%. To show the efficacy of the approach described herein, after the beam is delivered at the plurality of angles in step 518 using the aperture and beam intensity values at each angle, a comparison is made between the dose distribution of this MCO plan and a conventional clinical plan. FIG. 6B is a graph 610 that illustrates an example of coverage and conformity of target volumes, according to an embodiment. The horizontal axis 616 indicates the various target volume statistics, including the primary target volume, the high-risk target volume and the low-risk target volume and conformity. The vertical axis 614 indicates a percentage value that indicates one of a coverage percentage of the target volume receiving the prescription dose $PD_t$, or a conformity percentage of the target volume, defined below. The coverage percentage is defined as a percentage of the target volume that receives the prescription dose $PD_t$. The conformity percentage is defined as a ratio of a total volume that receives the prescription dose $PD_t$ (e.g. inside or outside of the target volume) to a volume of the target volume. Unlike the coverage percentage, which has a maximum value of 100%, the conformity percentage can exceed 100%. However, an ideal value of the conformity percentage is 100%, so to confine the prescription dose $PD_t$ within the target volume. The percentage coverage 618 for the primary target volume, the percentage coverage 620 for the high-risk target volume and the percentage coverage 622 for the low-risk target volume is substantially similar for the MCO (right bar in each statistic) and conventional clinical plans (left bar in each case). However, the percentage conformity 624 for the MCO plan (right bar) is much closer to 100% than the conventional clinical plan (left bar) and thus the MCO plan is much improved over the conventional clinical plan.

FIG. 6C is a graph 630 that illustrates an example of mean and max dosages of organs-at-risk, critical organ and normal tissue, according to an embodiment. The horizontal axis 636 indicates the various tissue type statistics, with the conventional clinical plan values given by the left bar and the MCO plan values given by the right bar for each statistic. The vertical axis 634 indicates the dose received at each tissue type in units of Gray (Gy). The left parotid mean dose 638 is approximately 20% lower in the MCO plan than in the conventional clinical plan. The right parotid mean dose 640 is approximately 30% lower in the MCO plan than the conventional clinical plan. The oral cavity mean dose 642 is approximately 40% lower in the MCO plan than the conventional clinical plan. The spinal cord maximum dose 644 is approximately 42% lower in the MCO plan than the conventional clinical plan. The brain stem maximum dose 646 is approximately 83% lower in the MCO plan than the conventional clinical plan. The normal tissue maximum dose 648 is approximately 4% lower in the MCO plan than the conventional clinical plan. Thus, with the exception of the normal tissue, the MCO plan advantageously provided a noticeably reduced dose relative to the conventional clinical plan.

Figure 6D:
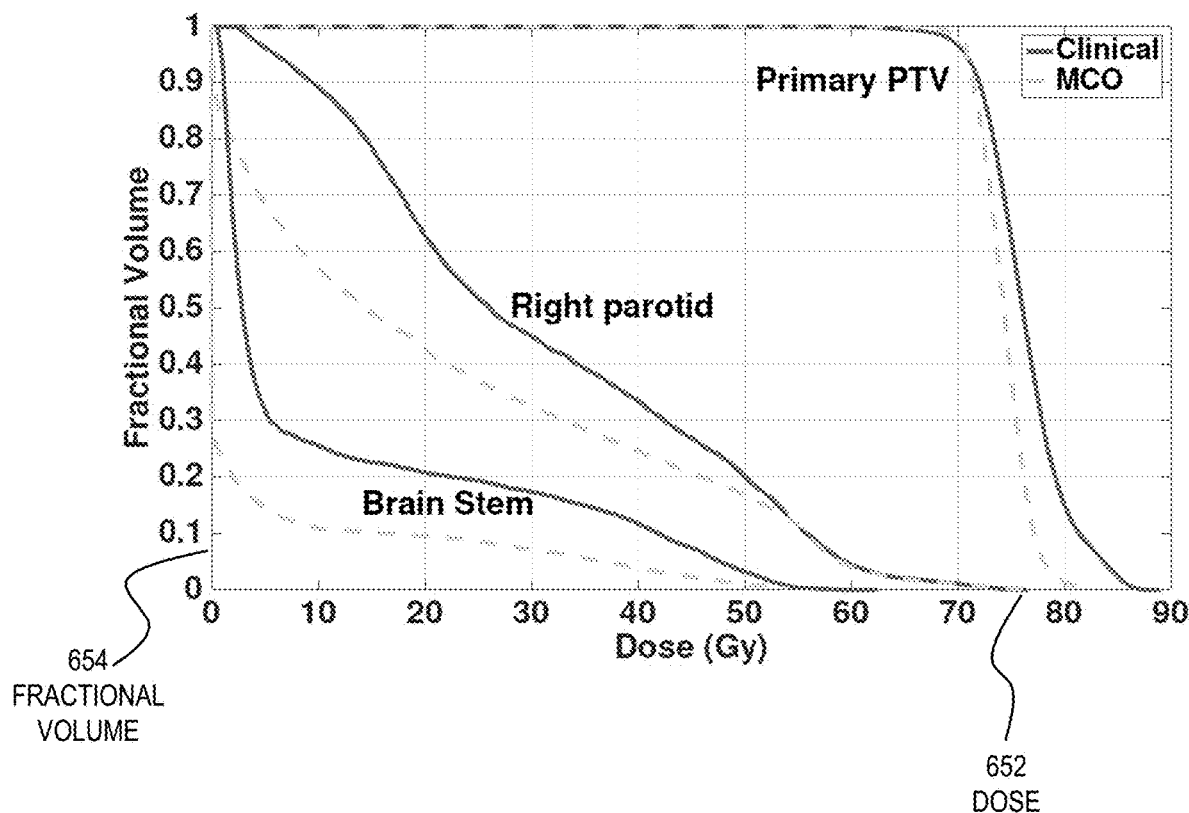
FIG. 6D is a graph that illustrates an example of fractional volume versus dosage for a target volume, an organ-at-risk and a critical organ, according to an embodiment.

FIG. 6D is a graph 650 that illustrates an example of fractional volume versus dosage for a primary target volume, the right parotid OAR and the brain stem, according to an embodiment. The horizontal axis 652 indicates the dose received in units of Gray (Gy). The vertical axis 654 indicates the fractional volume (unitless). Two curves are shown for each of the primary target volume, the right parotid OAR and the brain stem. The upper curve for each tissue type indicates the conventional clinical plan and the lower curve indicates the MCO plan. As can be seen, the MCO plan delivers much lower doses to the non target tissues (up to about 20 Gy lower), while essentially the same dose to 98% of the primary target tissue.

FIG. 6E is a graph 660 that illustrates an example of fractional volume versus dosage for a high-risk target volume and the left parotid OAR, according to an embodiment. The horizontal axis 662 indicates the dose received in units of Gray (Gy). The vertical axis 664 indicates the fractional volume (unitless). Two curves are shown for each of the high-risk target volume and the left parotid OAR. The lower curve for the left parotid type indicates the MCO plan and the upper curve indicates the conventional clinical plan. The upper curve for the high risk primary target type indicates the conventional clinical plan and the lower curve indicates the MCO plan. As can be seen, the MCO plan delivers lower doses to the left parotid (about 5 Gy or less), while essentially the same dose to 98% of the high risk primary target tissue FIG. 6F is a graph 670 that illustrates an example of fractional volume versus dosage for a low-risk target volume and the oral cavity OAR, according to an embodiment. The horizontal axis 672 indicates the dose received in units of Gray (Gy). The vertical axis 674 indicates the fractional volume (unitless). Two curves are shown for each of the low-risk target volume and the oral cavity OAR. The upper curve for each tissue type indicates the conventional clinical plan and the lower curve indicates the MCO plan. As can be seen, the MCO plan delivers much lower doses to the oral cavity (almost 20 Gy), while essentially the same dose to 98% of the low risk primary target tissue.

FIG. 6G is a graph 680 that illustrates an example of fractional volume versus dosage for a critical organ and normal tissue, according to an embodiment. The horizontal axis 682 indicates the dose received in units of Gray (Gy). The vertical axis 684 indicates the fractional volume (unitless). Two curves are shown for each of the spinal cord critical organ and normal tissue. The upper curve for each tissue type indicates the conventional clinical plan and the lower curve indicates the MCO plan. As can be seen, the MCO plan delivers much lower doses (about 10 Gy lower) to the spinal cord critical organ, while delivering somewhat lower doses (about 3 Gy lower) to the normal tissue.

The graphs of FIGS. 6D-6G indicate that both of the MCO and conventional clinical plans provide sufficient coverage (e.g. 95%) for all three of the target volumes. Additionally, the MCO plan outperformed the conventional clinical plan with respect to OAR, critical organ and normal tissue sparing. Additionally, the MCO plan provides a more uniform dose (e.g. percentage conformity closer to 100%) to the target volume than the conventional clinical plan.

3. Hardware Overview

FIG. 7 is a block diagram that illustrates a computer system 700 upon which an embodiment of the invention may be implemented. Computer system 700 includes a communication mechanism such as a bus 710 for passing information between other internal and external components of the computer system 700. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 700, or a portion thereof, constitutes a means for performing one or more steps of one or more methods described herein.

A sequence of binary digits constitutes digital data that is used to represent a number or code for a character. A bus 710 includes many parallel conductors of information so that information is transferred quickly among devices coupled to the bus 710. One or more processors 702 for processing information are coupled with the bus 710. A processor 702 performs a set of operations on information. The set of operations include bringing information in from the bus 710 and placing information on the bus 710. The set of operations also typically include comparing two or more units of information, shifting positions of units of information, and combining two or more units of information, such as by addition or multiplication. A sequence of operations to be executed by the processor 702 constitutes computer instructions.

Computer system 700 also includes a memory 704 coupled to bus 710. The memory 704, such as a random access memory (RAM) or other dynamic storage device, stores information including computer instructions. Dynamic memory allows information stored therein to be changed by the computer system 700. RAM allows a unit of information stored at a location called a memory address to be stored and retrieved independently of information at neighboring addresses. The memory 704 is also used by the processor 702 to store temporary values during execution of computer instructions. The computer system 700 also includes a read only memory (ROM) 706 or other static storage device coupled to the bus 710 for storing static information, including instructions, that is not changed by the computer system 700. Also coupled to bus 710 is a non-volatile (persistent) storage device 708, such as a magnetic disk or optical disk, for storing information, including instructions, that persists even when the computer system 700 is turned off or otherwise loses power.

Information, including instructions, is provided to the bus 710 for use by the processor from an external input device 712, such as a keyboard containing alphanumeric keys operated by a human user, or a sensor. A sensor detects conditions in its vicinity and transforms those detections into signals compatible with the signals used to represent information in computer system 700. Other external devices coupled to bus 710, used primarily for interacting with humans, include a display device 714, such as a cathode ray tube (CRT) or a liquid crystal display (LCD), for presenting images, and a pointing device 716, such as a mouse or a trackball or cursor direction keys, for controlling a position of a small cursor image presented on the display 714 and issuing commands associated with graphical elements presented on the display 714.

In the illustrated embodiment, special purpose hardware, such as an application specific integrated circuit (IC) 720, is coupled to bus 710. The special purpose hardware is configured to perform operations not performed by processor 702 quickly enough for special purposes. Examples of application specific ICs include graphics accelerator cards for generating images for display 714, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 700 also includes one or more instances of a communications interface 770 coupled to bus 710. Communication interface 770 provides a two-way communication coupling to a variety of external devices that operate with their own processors, such as printers, scanners and external disks. In general the coupling is with a network link 778 that is connected to a local network 780 to which a variety of external devices with their own processors are connected. For example, communication interface 770 may be a parallel port or a serial port or a universal serial bus (USB) port on a personal computer. In some embodiments, communications interface 770 is an integrated services digital network (ISDN) card or a digital subscriber line (DSL) card or a telephone modem that provides an information communication connection to a corresponding type of telephone line. In some embodiments, a communication interface 770 is a cable modem that converts signals on bus 710 into signals for a communication connection over a coaxial cable or into optical signals for a communication connection over a fiber optic cable. As another example, communications interface 770 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 770 sends and receives electrical, acoustic or electromagnetic signals, including infrared and optical signals, that carry information streams, such as digital data.

The term computer-readable medium is used herein to refer to any medium that participates in providing information to processor 702, including instructions for execution. Such a medium may take many forms, including, but not limited to, non-volatile media, volatile media and transmission media. Non-volatile media include, for example, optical or magnetic disks, such as storage device 708. Volatile media include, for example, dynamic memory 704. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 702, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 702, except for carrier waves and other signals.

Logic encoded in one or more tangible media includes one or both of processor instructions on a computer-readable storage media and special purpose hardware, such as ASIC *720.

Network link 778 typically provides information communication through one or more networks to other devices that use or process the information. For example, network link 778 may provide a connection through local network 780 to a host computer 782 or to equipment 784 operated by an Internet Service Provider (ISP). ISP equipment 784 in turn provides data communication services through the public, world-wide packet-switching communication network of networks now commonly referred to as the Internet 790. A computer called a server 792 connected to the Internet provides a service in response to information received over the Internet. For example, server 792 provides information representing video data for presentation at display 714.

The invention is related to the use of computer system 700 for implementing the techniques described herein. According to one embodiment of the invention, those techniques are performed by computer system 700 in response to processor 702 executing one or more sequences of one or more instructions contained in memory 704. Such instructions, also called software and program code, may be read into memory 704 from another computer-readable medium such as storage device 708. Execution of the sequences of instructions contained in memory 704 causes processor 702 to perform the method steps described herein. In alternative embodiments, hardware, such as application specific integrated circuit 720, may be used in place of or in combination with software to implement the invention. Thus, embodiments of the invention are not limited to any specific combination of hardware and software.

The signals transmitted over network link 778 and other networks through communications interface 770, carry information to and from computer system 700. Computer system 700 can send and receive information, including program code, through the networks 780, 790 among others, through network link 778 and communications interface 770. In an example using the Internet 790, a server 792 transmits program code for a particular application, requested by a message sent from computer 700, through Internet 790, ISP equipment 784, local network 780 and communications interface 770. The received code may be executed by processor 702 as it is received, or may be stored in storage device 708 or other non-volatile storage for later execution, or both. In this manner, computer system 700 may obtain application program code in the form of a signal on a carrier wave.

Various forms of computer readable media may be involved in carrying one or more sequence of instructions or data or both to processor 702 for execution. For example, instructions and data may initially be carried on a magnetic disk of a remote computer such as host 782. The remote computer loads the instructions and data into its dynamic memory and sends the instructions and data over a telephone line using a modem. A modem local to the computer system 700 receives the instructions and data on a telephone line and uses an infra-red transmitter to convert the instructions and data to a signal on an infra-red a carrier wave serving as the network link 778. An infrared detector serving as communications interface 770 receives the instructions and data carried in the infrared signal and places information representing the instructions and data onto bus 710. Bus 710 carries the information to memory 704 from which processor 702 retrieves and executes the instructions using some of the data sent with the instructions. The instructions and data received in memory 704 may optionally be stored on storage device 708, either before or after execution by the processor 702.

FIG. 8 illustrates a chip set 800 upon which an embodiment of the invention may be implemented. Chip set 800 is programmed to perform one or more steps of a method described herein and includes, for instance, the processor and memory components described with respect to FIG. *7 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 800, or a portion thereof, constitutes a means for performing one or more steps of a method described herein.

In one embodiment, the chip set 800 includes a communication mechanism such as a bus 801 for passing information among the components of the chip set 800. A processor 803 has connectivity to the bus 801 to execute instructions and process information stored in, for example, a memory 805. The processor 803 may include one or more processing cores with each core configured to perform independently. A multi-core processor enables multiprocessing within a single physical package. Examples of a multi-core processor include two, four, eight, or greater numbers of processing cores. Alternatively or in addition, the processor 803 may include one or more microprocessors configured in tandem via the bus 801 to enable independent execution of instructions, pipelining, and multithreading. The processor 803 may also be accompanied with one or more specialized components to perform certain processing functions and tasks such as one or more digital signal processors (DSP) 807, or one or more application-specific integrated circuits (ASIC) 809. A DSP 807 typically is configured to process real-world signals (e.g., sound) in real time independently of the processor 803. Similarly, an ASIC 809 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 803 and accompanying components have connectivity to the memory 805 via the bus 801. The memory 805 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 805 also stores the data associated with or generated by the execution of one or more steps of the methods described herein.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article. As used herein, unless otherwise clear from the context, a value is "about" another value if it is within a factor of two (twice or half) of the other value. While example ranges are given, unless otherwise clear from the context, any contained ranges are also intended in various embodiments. Thus, a range from 0 to 10 includes the range 1 to 4 in some embodiments.

What is claimed is:

1. A method comprising:
   determining a plurality of voxels in a reference frame of a radiation source that emits a beam of radiation at a plurality of angles with controlled intensity and beam cross sectional shape based on values of a plurality of apertures at each angle;
   setting an upper and lower bound on a plurality of objective functions that are each associated with a plurality of tissue types within a subject;
   defining a single objective function based on the plurality of objective functions, wherein the single objective function has parameters based on the upper and lower bound for each objective function and the plurality of apertures, and the parameters include the upper bound and a reciprocal of a difference between the upper bound and lower bound;
   determining a radiation dose delivered to the voxels of each tissue type based on minimizing the single objective function using an initial set of one or more apertures at each of the plurality of angles; and
   delivering the beam of radiation with controlled intensity and beam cross sectional shape at each angle based on the initial set of the one or more apertures at each angle where a value of the single objective function from said minimizing the single objective function using the initial set of one or more apertures is reduced from the value of the single objective function from minimizing the single objective function using a set of one or more apertures different from the initial set of one or more apertures.

2. A method as recited in claim 1, further comprising:
   determining for at least one angle a changed aperture based on the radiation dose delivered to the voxels at each tissue type; and
   minimizing the single objective function using the plurality of apertures with the changed aperture such that the value of the single objective function is reduced from the value of the single objective function determined from the minimizing the single objective function using the plurality of apertures without the changed aperture;
   wherein delivering the beam of radiation with controlled intensity and beam cross sectional shape at each angle using the plurality of apertures comprises delivering the beam of radiation with controlled intensity and beam cross sectional shape at each angle using the plurality of apertures with the changed aperture.

3. A method as recited in claim 1, wherein the plurality of tissue types includes a target tissue type and wherein the minimizing of the single objective function is constrained such that a prescription dose is delivered to a minimum percentage of the target tissue type.

4. A method as recited in claim 1, wherein the plurality of tissue types includes an organ-at-risk (OAR) tissue type and wherein the minimizing of the single objective function is constrained such that a threshold dose is delivered to a maximum percentage of the OAR tissue type.

5. A method as recited in claim 1, wherein the determining the plurality of voxels is performed by one of an X-ray Computed tomography (CT) scanner or an nuclear magnetic resonance imagery (MRI) scanner.

6. A method as recited in claim 1, further comprising moving metal leaves along channels within a multi-leaf collimator (MLC) positioned between the radiation source and the subject at each angle to adjust the values of the plurality of apertures.

7. A method as recited in claim 1, wherein the plurality of tissue types include a target tissue type and wherein the objective function associated with the target tissue type is a maximum variation between a prescription dose and the radiation dose delivered to the voxels of the target tissue type.

8. A method as recited in claim 1, wherein the plurality of tissue types include a target tissue type and wherein the objective function associated with the target tissue type is a minimum dose delivered to the voxels of the target tissue type.

9. A method as recited in claim 1, wherein the plurality of tissue types include an organ at risk (OAR) tissue type and wherein the objective function associated with the OAR tissue type is a mean dose delivered to the voxels of the OAR tissue type.

10. A method as recited in claim 1, wherein the plurality of tissue types include a critical organ tissue type and wherein the objective function associated with the critical organ tissue type is a maximum dose delivered to the voxels of the critical organ tissue type.

11. A method as recited in claim 1, wherein the plurality of tissue types include a target tissue type, an organ at risk (OAR) tissue type, a critical organ tissue type and a normal tissue type, wherein the objective function associated with the normal tissue type is a maximum dose delivered to the voxels of the normal tissue type.

12. A method as recited in claim 1, wherein the defining of the single objective function is further based on an intensity value of the beam of radiation at one or more apertures at each of the plurality of angles and wherein the minimizing of the single objective function is performed using an initial set of intensity values of the beam of radiation.

13. A non-transitory computer-readable medium carrying one or more sequences of instructions, wherein execution of the one or more sequences of instructions by one or more processors causes the one or more processors to perform the steps of:
  determining a plurality of voxels in a reference frame of a radiation source that emits a beam of radiation at a plurality of angles with controlled intensity and beam cross sectional shape based on values of a plurality of apertures at each angle;
  defining a single objective function based on a plurality of objective functions that are each associated with a plurality of tissue types within a subject, wherein the single objective function has parameters based on an upper and lower bound of the plurality of objective functions and the plurality of apertures, and the parameters include the upper bound and a reciprocal of a difference between the upper bound and lower bound;
  determining a radiation dose delivered to the voxels of each tissue type based on minimizing the single objective function using an initial set of one or more apertures at each of the plurality of angles; and
  delivering the beam of radiation with controlled intensity and beam cross sectional shape at each angle based on the initial set of one or more apertures at each angle where a value of the single objective function from said minimizing the single objective function using the initial set of one or more apertures is reduced from the value of the single objective function from minimizing the single objective function using a set of one or more apertures different from the initial set of one or more apertures.

14. A non-transitory computer-readable medium as recited in claim 13, wherein execution of the one or more sequences of instructions by one or more processors further causes the one or more processors to perform the steps of:
  determining for at least one angle a changed aperture based on the radiation dose delivered to the voxels at each tissue type; and
  minimizing the single objective function using the plurality of apertures with the changed aperture such that the value of the single objective function is reduced from the value of the single objective function determined from the minimizing of the single objective function using the plurality of apertures without the changed aperture;
  wherein delivering the beam of radiation with controlled intensity and beam cross sectional shape at each angle using the plurality of apertures comprises delivering the beam of radiation with controlled intensity and beam cross sectional shape at each angle using the plurality of apertures with the changed aperture.

15. A system comprising:
  a radiation source to emit a beam of radiation at a plurality of angles to each voxel of a plurality of voxels comprising a reference frame of the radiation source;
  a plurality of apertures with values at each angle to control an intensity and cross sectional shape of the beam of radiation at each voxel in the reference frame;
  at least one processor; and
  at least one memory including one or more sequence of instructions;
  the at least one memory and the one or more sequence of instructions configured to, with the at least one processor, cause the at least one processor to;
    define a single objective function based on a plurality of objective functions that are each associated with a plurality of tissue types within a subject, wherein the single objective function has parameters based on an upper and lower bound of the plurality of objective functions and the plurality of apertures, and the parameters include the lower bound and a reciprocal of a difference between the upper bound and lower bound;
    determine a radiation dose delivered to the voxels of each tissue type based on minimizing the single objective function using an initial set of one or more apertures at each of the plurality of angles; and
    deliver the beam of radiation with controlled intensity and beam cross sectional shape at each angle based on the initial set of one or more apertures at each angle where a value of the single objective function from said minimizing the single objective function using the initial set of one or more apertures is reduced from the value of the single objective function from minimizing the single objective function using a set of one or more apertures different from the initial set of one no more apertures.

16. A system as recited in claim 15, wherein the at least one memory and the one or more sequence of instructions are configured to, with the at least one processor, further cause the at least one processor to:
  determine for at least one angle a changed aperture based on the radiation dose delivered to the voxels of each tissue type; and
  minimize the single objective function using the plurality of apertures with the changed aperture such that the value of the single objective function is reduced from the value of the single objective function determined from the minimizing of the single objective function using the plurality of apertures without the changed aperture;
  wherein delivery of the beam of radiation with controlled intensity and beam cross sectional shape at each angle using the plurality of apertures comprises delivery of the beam of radiation with controlled intensity and beam cross sectional shape at each angle using the plurality of apertures with the changed aperture.

17. A system as recited in claim 15, wherein the single objective function is defined based on a sum of the plurality of objective functions, wherein the plurality of tissue types includes a target tissue type and wherein the at least one memory and the one or more sequences of instructions are configured to cause the at least one processor to minimize the sum of the plurality of objective functions such that a prescription dose is delivered to a minimum percentage of the target tissue type.

18. A system as recited in claim 15, further comprising an imaging system to obtain measurements related to the plurality of tissue type within a volume of the subject that encompasses the plurality of voxels, wherein the imaging system is one of an X-ray Computed tomography (CT) scanner or an nuclear magnetic resonance imagery (MRI) scanner.

19. A system as recited in claim 15, further comprising a multi-leaf collimator (MLC) positioned between the radiation source and the subject, including leaves configured to move within channels to adjust the values of the plurality of apertures at each angle.

* * * * *